(12) United States Patent
Kastler et al.

(10) Patent No.: US 8,404,844 B2
(45) Date of Patent: Mar. 26, 2013

(54) PERYLENE SEMICONDUCTORS AND METHODS OF PREPARATION AND USE THEREOF

(75) Inventors: Marcel Kastler, Basel (CH); Subramanian Vaidyanathan, Singapore (SG); Florian Doetz, Singapore (SG); Silke Annika Koehler, Basel (CH); He Yan, Skokie, IL (US); Antonio Facchetti, Chicago, IL (US); Shaofeng Lu, Skokie, IL (US); Yan Zheng, Skokie, IL (US)

(73) Assignees: BASF SE, Ludwigshafen (DE); Polyera Corporation, Princeton, NJ (US)

( * ) Notice: Subject to any disclaimer, the term of this patent is extended or adjusted under 35 U.S.C. 154(b) by 199 days.

(21) Appl. No.: 12/866,331

(22) PCT Filed: Feb. 5, 2009

(86) PCT No.: PCT/EP2009/051313
§ 371 (c)(1),
(2), (4) Date: Aug. 5, 2010

(87) PCT Pub. No.: WO2009/098252
PCT Pub. Date: Aug. 13, 2009

(65) Prior Publication Data
US 2010/0319778 A1 Dec. 23, 2010

Related U.S. Application Data

(60) Provisional application No. 61/026,311, filed on Feb. 5, 2008.

(51) Int. Cl.
*C07D 471/08* (2006.01)
*H01L 51/50* (2006.01)
*H01L 29/02* (2006.01)
(52) U.S. Cl. .............................. 546/37; 313/498; 257/40
(58) Field of Classification Search .................... 546/37; 257/40; 313/498
See application file for complete search history.

(56) References Cited

U.S. PATENT DOCUMENTS

| | | | |
|---|---|---|---|
| 6,491,749 B1 * | 12/2002 | Langhals et al. ......... | 106/287.21 |
| 7,569,693 B2 | 8/2009 | Marks et al. | |
| 7,671,202 B2 | 3/2010 | Marks et al. | |
| 7,892,454 B2 | 2/2011 | Facchetti et al. | |
| 7,893,265 B2 | 2/2011 | Facchetti et al. | |
| 7,902,363 B2 | 3/2011 | Facchetti et al. | |
| 7,947,837 B2 | 5/2011 | Marks et al. | |
| 7,982,039 B2 | 7/2011 | Marks et al. | |
| 8,022,214 B2 | 9/2011 | Facchetti et al. | |
| 2008/0177073 A1 | 7/2008 | Facchetti et al. | |
| 2008/0185577 A1 | 8/2008 | Facchetti et al. | |

OTHER PUBLICATIONS

Nolde, F. et al.: Synthesis and self-organization of core-extended perylene tetracarboxdiimides with branched alkyl substitution. Chem. Mater., vol. 18, pp. 3715-3725, 2006.*
Rajasingh, P. et al.: Selective bromination of Perylene diimides under mild conditions. J. Org. Chem., vol. 72, pp. 5973-5979, 2007.*
Osswald, P. et al.: Effects of bay substituents on the racemitization barriers of Perylene bisimides: Resolution of atropo-enantiomers. J. Am. Chem. Soc., vol. 129, pp. 14319-14326, 2007.*
U.S. Appl. No. 13/266,935, filed Oct. 28, 2011, Karpov, et al.
U.S. Appl. No. 13/128,961, filed May 12, 2011, Quinn, et al.
International Search Report issued May 27, 2009 in PCT/EP09/051313 filed Feb. 5, 2009.
Jones, B. A. et al., "Tuning Orbital Energetics in Arylene Diimide Semiconductors, Materials Design for Ambient Stability of n-Type Charge Transport", Journal of the American Chemical Society, vol. 129, No. 49, pp. 15259-15278, XP002526266 (Jan. 1, 2007).
Jones, B. A. et al., "High-Mobility Air-Stable n-Type Semiconductors With Processing Versatility: Dicyanoperylene-3,4:9,10-bis (dicarboximides)", Angewandte Chemie International Edition, vol. 43, pp. 6363-6366, XP002526265 (Jan. 1, 2004).
Jung, T. et al., "Nanoscale n-channel and ambipolar Organic Field-Effect Transistors", Applied Physics Letters, vol. 88 No. 18, pp. 183102-1-183102-3, XP 012081437, ISSN: 0003-6951, (May 1, 2006).
Chen, Z. et al., "Tetrachloro-Substituted Perylene Bisimide Dyes As Promising n-Type Organic Semiconductors: Studies on Structural, Electrochemical and Charge Transport Properties", CHEMPHYSCHEM, vol. 5, pp. 137-140, XP002501245, ISSN: 1439-4235, (Jan. 1, 2004).
Wuerthner, F. et al., "Synthesis and Optical and Electrochemical Properties of Core-Fluorinated Perylene Bisimides", Organic Letters, vol. 8, No. 17, pp. 3765-3768, XP 002430943, ISSN: 1523-7060, (Jul. 25, 2006).
Debije, M. G. et al., "Dramatic Increase in Charge Carrier Lifetime in a Liquid Crystalline Perylene Bisimide Derivative Upon Bay Substitution with Chlorine", Journal of Materials Chemistry, vol. 15, pp. 1270-1276, XP 002526946, (Jan. 25, 2005).
Katz, H. E. et al., "A Soluble and Air-Stable Organic Semiconductor With High Electron Mobility", Letters to Nature, Nature, vol. 404, pp. 478-481, (Mar. 30, 2000).
Yoo, B. et al., "Organic Complementary D Flip-Flops Enabled by Perylene Diimides and Pentacene", IEEE Electron Device Letters, vol. 27, No. 9, pp. 737-739, ISSN 0741-3106, (Sep. 2006).
Han, W.-G. et al., "Density Functional Studies of the Ground-And Excited-State Potential-Energy Curves of Stilbene cis-trans Isomerization", Chemphyschem, vol. 3, pp. 167-178, (
Katz, H. E. et al., "Naphthalenetetracarboxylic Diimide-Based n-Channel Transistor Semiconductors: Structural Variation and Thiol-Enhanced Gold Contacts", J. Am. Chem. Soc., vol. 122, No. 32, pp. 7787-7792, (2000).

(Continued)

*Primary Examiner* — Charanjit Aulakh
(74) *Attorney, Agent, or Firm* — Oblon, Spivak, McClelland, Maier & Neustadt, L.L.P.

(57) ABSTRACT

The present invention relates to semiconducting compounds, materials prepared from such compounds, methods of preparing such compounds and semiconductor materials, as well as various compositions, composites, and devices that incorporate the compounds and semiconductor materials. The semiconducting compounds can have higher electron-transport efficiency and higher solubility in common solvents compared to related representative compounds.

57 Claims, 5 Drawing Sheets

OTHER PUBLICATIONS

Yoon, M-H, et al., "Organic Thin-Film Transistors Based on Carbonyl-Functionalized Quaterthiophenes: High Mobility N-Channel Semiconductors and Ambipolar Transport", J. Am. Chem. Soc., vol. 127, No. 5, pp. 1348-1349, (2005). 2002).

Yuan, J. et al., "Study on the Instability of Organic Field-Effect Transistors Based on Fluorinated Copper Phthalocyanine", Thin Solid Films, vol. 450, pp. 316-319, (2004).

Tong, W. Y. et al., "Metal Phthalocyanine Nanoribbons and Nanowires", J. Phys. Chem. B, vol. 110, No. 35, pp. 17406-17413, (2006).

U.S. Appl. No. 61/057,547, filed May 30, 2008, Facchetti, et al.
U.S. Appl. No. 61/026,311, filed Feb. 5, 2008, Kastler, et al.
U.S. Appl. No. 61/026,322, filed Feb. 5, 2008, Facchetti, et al.
U.S. Appl. No. 61/050,010, filed May 2, 2008, Chen, et al.
U.S. Appl. No. 61/088,215, filed Aug. 12, 2008, Facchetti, et al.
U.S. Appl. No. 61/088,236, filed Aug. 12, 2008, Facchetti, et al.
U.S. Appl. No. 61/088,246, filed Aug. 12, 2008, Facchetti, et al.
U.S. Appl. No. 60/859,761, filed Nov. 17, 2006, Facchetti, et al.
U.S. Appl. No. 60/879,145, filed Jan. 8, 2007, Facchetti, et al.

* cited by examiner

PERYLENE SEMICONDUCTORS AND METHODS OF PREPARATION AND USE THEREOF

CROSS REFERENCE TO RELATED APPLICATION

This application claims priority to and the benefit of U.S. Provisional Patent Application Ser. No. 61/026,311, filed on Feb. 5, 2008, the disclosure of which is incorporated by reference herein in its entirety.

BACKGROUND

Recent developments in organic-based light-emitting diodes (OLEDs), photovoltaics (OPVs), and field-effect transistors (OFETs) have opened up many opportunities in the field of organic electronics. One of the challenges in this field is to develop thin film devices that have environmentally stable electron-transporting (n-type) organic semiconductors with high-mobility. The performance and stability of organic n-type materials have significantly lagged behind their p-type counterparts. Some challenges for advancing the technology of organic n-type materials include their vulnerability to ambient conditions (e.g., air) and solution-processability. For example, it is desirable for these materials to be soluble in common solvents so that they can be formulated into inks for inexpensive printing processes.

The most common air-stable n-type organic semiconductors include perfluorinated copper phthalocyanine ($CuF_{16}Pc$), fluoroacyl oligothiophenes (e.g., DFCO-4TCO), N,N'-fluorocarbon-substituted naphthalene diimides (e.g., NDI-F, NDI-XF), cyano-substituted perylene diimides (e.g., PDI-FCN$_2$), and cyano-substituted naphthalene diimides (e.g., NDI-8CN$_2$). See, e.g., Bao et al. (1998), *J. Am. Chem. Soc.*, 120: 207-208; de Oteyza et al. (2005), *Appl. Phys. Lett.*, 87: 183504; Schön et al. (2000), *Adv Mater.* 12: 1539-1542; Ye et al. (2005), *Appl. Phys. Lett.*, 86: 253505; Yoon et al. (2006), *J. Am. Chem. Soc.*, 128: 12851-12869; Tong et al. (2006), *J. Phys. Chem. B.*, 110: 17406-17413; Yuan et al. (2004), *Thin Solid Films*, 450: 316-319; Yoon et al. (2005), *J. Am. Chem. Soc.*, 127: 1348-1349; Katz et al. (2000), *J. Am. Chem. Soc.*, 122: 7787-7792; Katz et al. (2000), *Nature (London)*, 404: 478-481; Katz et al (2001), *Chem. Phys. Chem.*, 3: 167-172; Jung et al. (2006), *Appl. Phys. Lett.*, 88: 183102; Yoo et al. (2006), *IEEE Electron Device Lett.*, 27: 737-739; Jones et al. (2004), *Angew. Chem., Int. Ed. Engl.*, 43: 6363-6366; and Jones et al. (2007), *J. Am. Chem. Soc.*, 129: 15259-15278. Rylene imides are particularly attractive because of their robust nature, flexible molecular orbital energetics, and excellent charge transport properties. However, high-mobility rylene compounds, including PDI-FCN$_2$ and NDI-F, have poor solubility. Soluble rylene compounds, on the other hand, usually have poor charge transport properties.

Accordingly, given potential applications in inexpensive and large-area organic electronics that can be produced by high-throughput reel-to-reel manufacture, the art desires new organic n-type semiconducting compounds, especially those possessing desirable properties such as air stability, high charge transport efficiency, and good solubility in common solvents.

SUMMARY

In light of the foregoing, the present teachings provide compounds that can be utilized as organic semiconductors and related materials, compositions, composites, and/or devices that can address various deficiencies and shortcomings of the state-of-the-art, including those outlined above.

More specifically, the present teachings provide 1-alkyl substituted alkyl nitrogen-functionalized perylene diimide compounds and derivatives which have semiconducting activity. Materials prepared from these compounds have demonstrated unexpected properties and results. For example, it has been discovered that, when compared to related representative compounds, compounds of the present teachings can have higher carrier mobility and/or better current modulation characteristics in field-effect devices (e.g., thin-film transistors). In addition, it has been discovered that compounds of the present teachings can possess certain processing advantages compared to related representative compounds such as better solubility to permit solution-processability and/or good stability at ambient conditions, for example, air stability. Further, the compounds can be embedded with other components for utilization in a variety of semiconductor-based devices.

In various embodiments, compounds of the present teachings can have formula I:

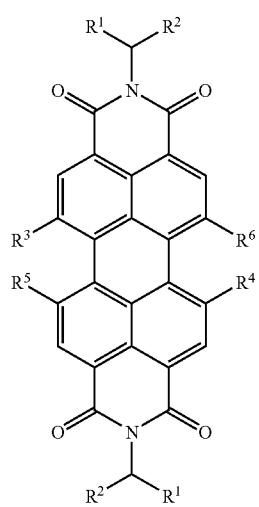

wherein $R^1$, $R^2$, $R^3$, $R^4$, $R^5$, and $R^6$ are as defined herein.

The present teachings also provide methods of preparing such compounds and semiconductor materials, as well as various compositions, composites, and devices that incorporate the compounds and semiconductor materials disclosed herein.

The foregoing as well as other features and advantages of the present teachings will be more fully understood from the following figures, description, and claims.

BRIEF DESCRIPTION OF THE DRAWINGS

It should be understood that the drawings described below are for illustration purposes only and are not necessarily to scale. The drawings are not intended to limit the scope of the present teachings in any way.

DETAILED DESCRIPTION

Figure 1:
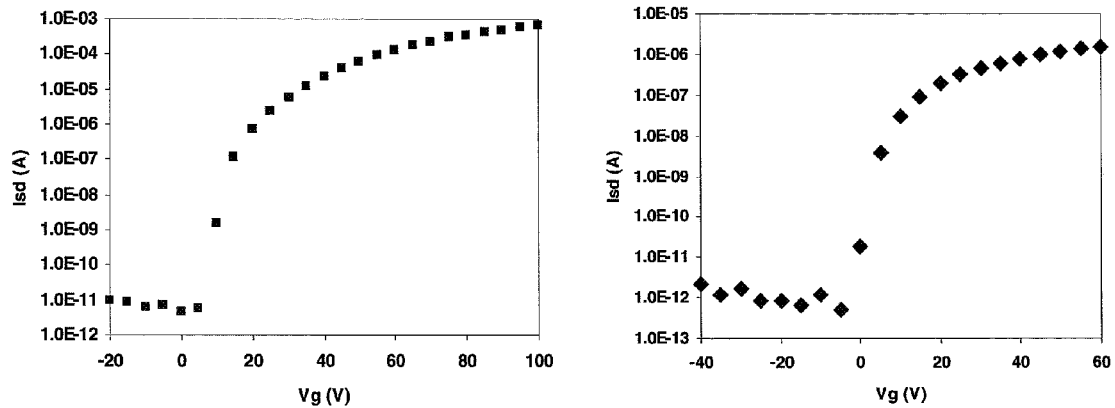
FIG. 1 shows representative transfer plots of certain embodiments of thin film transistor devices fabricated with compounds of the present teachings, where the thin film transistor devices include vacuum vapor-deposited (left) and solution-deposited (right) films of PDI1MP-CN$_2$ as the semiconductor layer.
Figure 2:
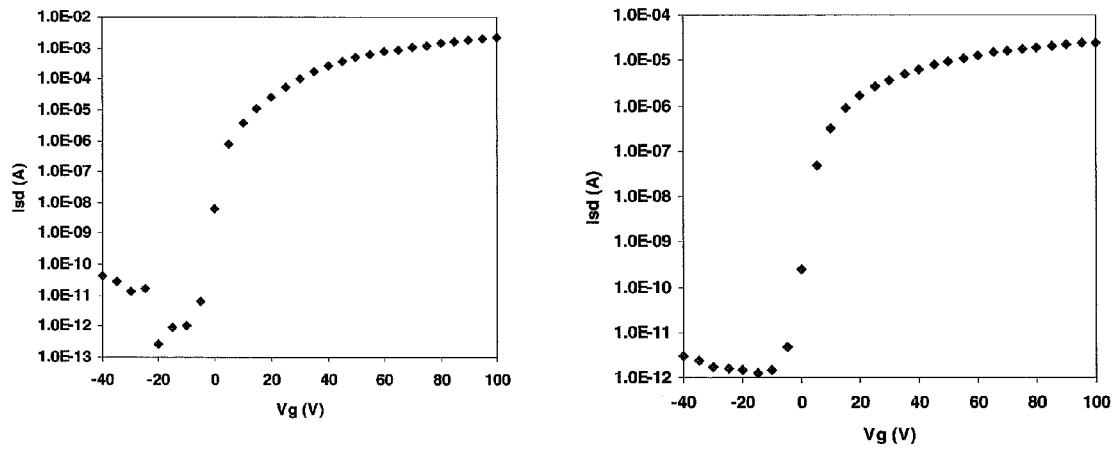
FIG. 2 shows representative transfer plots of certain embodiments of thin film transistor devices fabricated with compounds of the present teachings, where the thin film transistor devices include vacuum vapor-deposited (left) and solution-deposited (right) films of PDI1MB-CN$_2$ as the semiconductor layer.
Figure 3:
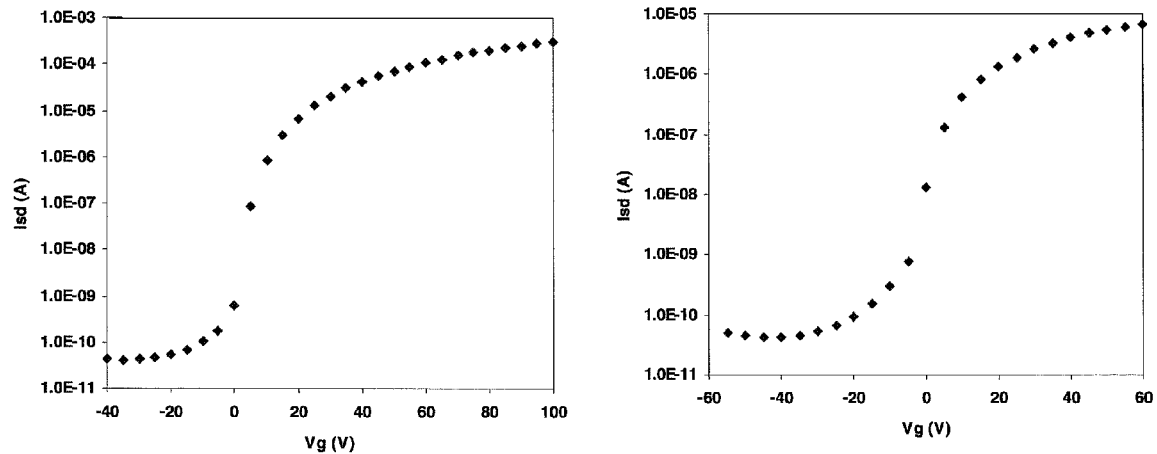
FIG. 3 shows representative transfer plots of certain embodiments of thin film transistor devices fabricated with compounds of the present teachings, where the thin film transistor devices include vacuum vapor-deposited (left) and solution-deposited (right) films of PDI1MPr—CN$_2$ as the semiconductor layer.
Figure 4:
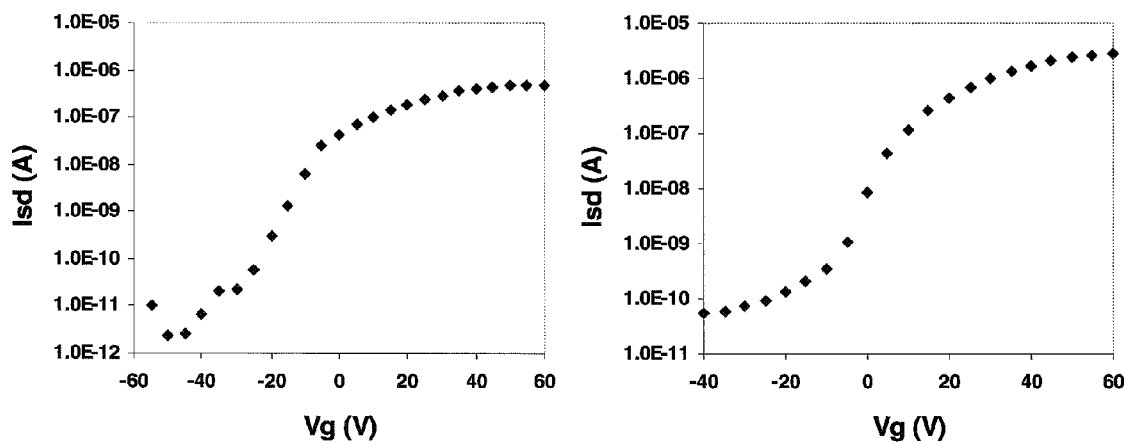
FIG. 4 shows representative transfer plots of certain embodiments of thin film transistor devices fabricated with compounds of the present teachings, where the thin film transistor devices include solution-deposited films of PDI1EB-CN$_2$ (left) and PDI1EPr—CN$_2$ (right) as the semiconductor layer.
Figure 5:
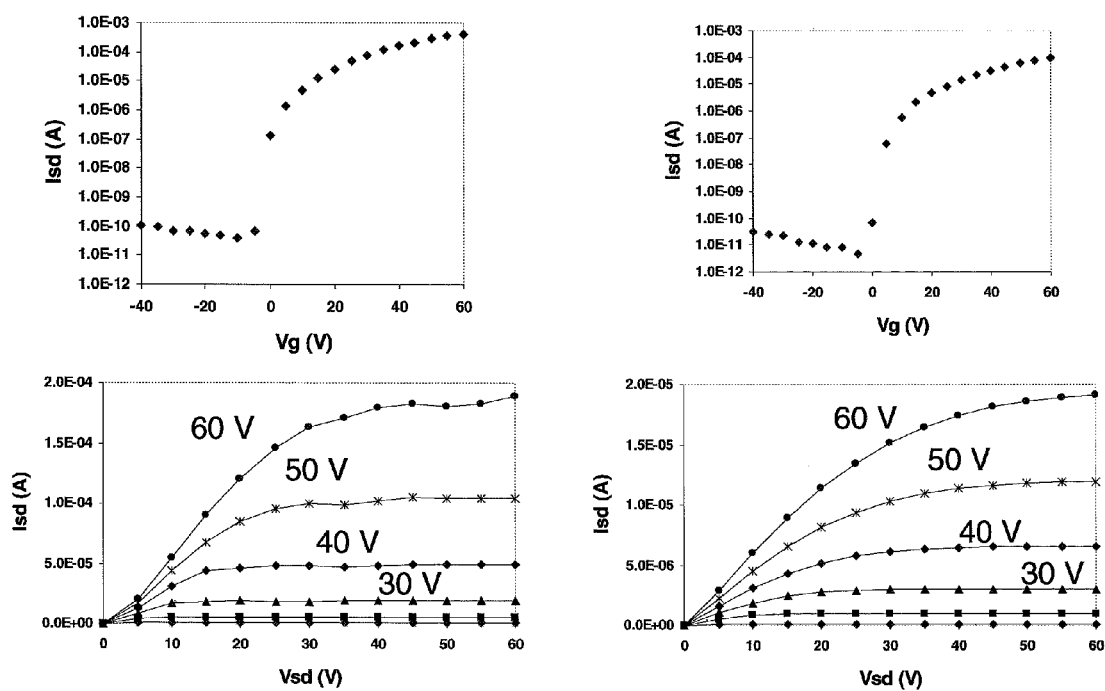
FIG. 5 shows representative transfer (top) and output (bottom) plots of certain embodiments of thin film transistor devices fabricated with compounds of the present teachings, where the thin film transistor devices include vapor-deposited films of PDI1EB-CN$_2$ grown at 110° C. (left) and at room temperature (right).

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value.

It should be understood that the order of steps or order for performing certain actions is immaterial so long as the present teachings remain operable. Moreover, two or more steps or actions may be conducted simultaneously.

As used herein, "halo" or "halogen" refers to fluoro, chloro, bromo, and iodo.

As used herein, "alkoxy" refers to —O-alkyl group. Examples of alkoxy groups include, but are not limited to, methoxy, ethoxy, propoxy (e.g., n-propoxy and isopropoxy), t-butoxy groups, and the like. The alkyl group in the —O-alkyl group can be substituted as described herein.

As used herein, "alkylthio" refers to an —S-alkyl group. Examples of alkylthio groups include, but are not limited to, methylthio, ethylthio, propylthio (e.g., n-propylthio and isopropylthio), t-butylthio groups, and the like. The alkyl group in the —S-alkyl group can be substituted as described herein.

As used herein, "oxo" refers to a double-bonded oxygen (i.e., =O).

As used herein, "alkyl" refers to a straight-chain or branched saturated hydrocarbon group. Examples of alkyl groups include methyl (Me), ethyl (Et), propyl (e.g., n-propyl and isopropyl), butyl (e.g., n-butyl, isobutyl, s-butyl, t-butyl), pentyl groups (e.g., n-pentyl, isopentyl, neopentyl), and the like. An alkyl group can have 1 to 30 carbon atoms, for example 1 to 20 carbon atoms (i.e., $C_{1-20}$ alkyl group). A lower alkyl group typically has up to 4 carbon atoms. Examples of lower alkyl groups include methyl, ethyl, propyl (e.g., n-propyl and isopropyl), and butyl groups (e.g., n-butyl, isobutyl, s-butyl, t-butyl). In some embodiments, alkyl groups can be substituted as disclosed herein.

As used herein, "haloalkyl" refers to an alkyl group having one or more halogen substituents. A haloalkyl group can have 1 to 30 carbon atoms, for example 1 to 10 carbon atoms (i.e., $C_{1-10}$ haloalkyl group). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups wherein all of the hydrogen atoms are replaced with halogen atoms (e.g., $CF_3$ and $C_2F_5$), are included within the definition of "haloalkyl." For example, a $C_{1-20}$ haloalkyl group can have the formula —$C_aH_{2a+1-b}X_b$, wherein X, at each occurrence, is F, Cl, Br, or I, a is an integer in the range of 1 to 20, and b is an integer in the range of 1 to 41, provided that b is not greater than 2a+1.

As used herein, "alkenyl" refers to a straight-chain or branched alkyl group having one or more carbon-carbon double bonds. In various embodiments, an alkenyl group can have 2 to 30 carbon atoms, for example, 2 to 10 carbon atoms (i.e., $C_{2-10}$ alkenyl group). Examples of alkenyl groups include, but are not limited to, ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In some embodiments, alkenyl groups can be substituted as disclosed herein.

As used herein, "alkynyl" refers to a straight-chain or branched alkyl group having one or more triple carbon-carbon bonds. Examples of alkynyl groups include ethynyl, propynyl, butynyl, pentynyl, and the like. The one or more triple carbon-carbon bonds can be internal (such as in 2-butyne) or terminal (such as in 1-butyne). In various embodiments, an alkynyl group can have 2 to 30 carbon atoms, for example, 2 to 10 carbon atoms (i.e., $C_{2-10}$ alkynyl group). In some embodiments, alkynyl groups can be substituted as disclosed herein.

As used herein, a "cyclic moiety" can include one or more (e.g., 1-6) carbocyclic or heterocyclic rings. The cyclic moiety can be a cycloalkyl group, a heterocycloalkyl group, an aryl group, or a heteroaryl group (i.e., can include only saturated bonds, or can include one or more unsaturated bonds regardless of aromaticity), each including, for example, 3-22 ring atoms, and can be optionally substituted as described herein. In embodiments where the cyclic moiety is a "monocyclic moiety," the "monocyclic moiety" can include a 3-14 membered aromatic or non-aromatic, carbocyclic or heterocyclic ring. A monocyclic moiety can include, for example, a phenyl group or a 5- or 6-membered heteroaryl group, each of which can be optionally substituted as described herein. In embodiments where the cyclic moiety is a "polycyclic moiety," the "polycyclic moiety" can include two or more rings fused to each other (i.e., sharing a common bond) and/or connected to each other via a spiro atom, or one or more bridged atoms. A polycyclic moiety can include an 8-22 membered aromatic or non-aromatic, carbocyclic or heterocyclic ring, such as a $C_{8-22}$ aryl group or an 8-22 membered heteroaryl group, each of which can be optionally substituted as described herein.

As used herein, "cycloalkyl" refers to a non-aromatic carbocyclic group including cyclized alkyl, alkenyl, and alkynyl groups. In various embodiments, a cycloalkyl group can have 3 to 22 carbon atoms, for example, 3 to 14 carbon atoms (i.e., $C_{3-14}$ cycloalkyl group). A cycloalkyl group can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Examples of cycloalkyl groups include, but are not limited to, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like. In some embodiments, cycloalkyl groups can be substituted as disclosed herein.

As used herein, "heteroatom" refers to an atom of any element other than carbon or hydrogen and includes, for example, nitrogen, oxygen, silicon, sulfur, phosphorus, and selenium.

As used herein, "cycloheteroalkyl" refers to a non-aromatic cycloalkyl group that contains at least one ring heteroatom selected from O, S, Se, N, P, and Si (e.g., O, S, and N), and optionally contains one or more double or triple bonds. A cycloheteroalkyl group can have 3 to 22 ring atoms, for example, 3 to 14 ring atoms (i.e., 3-14 membered cycloheteroalkyl group). One or more N, P, S, or Se atoms (e.g., N or S) in a cycloheteroalkyl ring may be oxidized (e.g., morpholine N-oxide, thiomorpholine S-oxide, thiomorpholine S,S-dioxide). In some embodiments, nitrogen or phosphorus atoms of cycloheteroalkyl groups can bear a substituent, for example, a hydrogen atom, an alkyl group, or other substituents as described herein. Cycloheteroalkyl groups can also contain one or more oxo groups, such as oxopiperidyl, oxooxazolidyl, dioxo-(1H,3H)-pyrimidyl, oxo-2(1H)-pyridyl, and the like. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothiophenyl, piperidinyl, piperazinyl, and the like. In some embodiments, cycloheteroalkyl groups can be substituted as disclosed herein.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have from 6 to 22 ring atoms in its ring system, for example, 6 to 14 ring atoms (i.e., $C_{6-14}$ aryl group), which can include multiple fused rings. In some embodiments, a polycyclic aryl group can have from 8 to 22 carbon atoms. Any suitable ring position of the aryl group can be covalently linked to the defined chemical structure. Examples of aryl groups having only aromatic carbocyclic ring(s) include, but are not limited to, phenyl, 1-naphthyl (bicyclic), 2-naphthyl (bicyclic), anthracenyl (tricyclic), phenanthrenyl (tricyclic) and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include, but are not limited to, benzodioxanyl, benzodioxolyl, chromanyl, indolinyl groups, and the like. In some embodiments, aryl groups can be substituted as disclosed herein. In some embodiments, an aryl group can have one or more halogen substituents and can be referred to as a "haloaryl" group. Perhaloaryl groups, i.e., aryl groups where all of the hydrogen atoms are replaced with halogen atoms (e.g., —$C_6F_5$), are included within the definition of "haloaryl." In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from O, N, S, Si, and Se or a polycyclic ring system where at least one of the rings present in the ring system is aromatic and contains at least one ring heteroatom. Polycyclic heteroaryl groups include two or more heteroaryl rings fused together and monocyclic heteroaryl rings fused to one or more aromatic carbocyclic rings, non-aromatic carbocyclic rings, and/or non-aromatic cycloheteroalkyl rings. A heteroaryl group, as a whole, can have, for example, from 5 to 22 ring atoms (e.g., 5-14 membered heteroaryl group) and contain 1-5 ring heteroatoms. The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5- or 6-membered monocyclic and 5-6 bicyclic ring systems shown below:

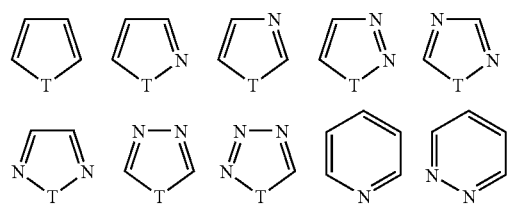

-continued

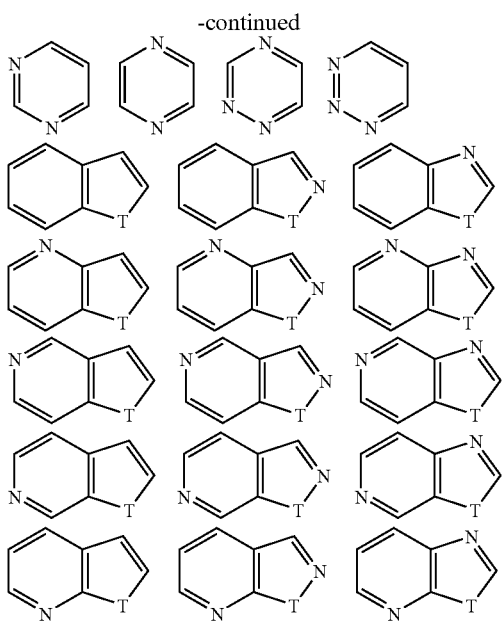

where T is O, S, NH, N-alkyl, N-aryl, N-(arylalkyl) (e.g., N-benzyl), SiH$_2$, SiH-(alkyl), Si(alkyl)$_2$, SiH-(arylalkyl), Si-(arylalkyl)$_2$, or Si(alkyl)(arylalkyl). Examples of heteroaryl groups include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl, and the like. Further examples of heteroaryl groups include, but are not limited to, 4,5,6,7-tetrahydroindolyl, tetrahydroquinolyl, benzothienopyridyl, benzofuropyridyl, and the like. In some embodiments, heteroaryl groups can be substituted as disclosed herein.

Compounds of the present teachings can include a "divalent group" defined herein as a linking group capable of forming a covalent bond with two other moieties. For example, compounds of the present teachings can include a divalent C$_{1-20}$ alkyl group, such as, for example, a methylene group.

At various places in the present specification, substituents of compounds are disclosed in groups or ranges. It is specifically intended that the description include each and every individual subcombination of the members of such groups and ranges. For example, the term "C$_{1-6}$ alkyl" is specifically intended to individually disclose C$_1$, C$_2$, C$_3$, C$_4$, C$_5$, C$_6$, C$_1$-C$_6$, C$_1$-C$_5$, C$_1$-C$_4$, C$_1$-C$_3$, C$_1$-C$_2$, C$_2$-C$_6$, C$_2$-C$_5$, C$_2$-C$_4$, C$_2$-C$_3$, C$_3$-C$_6$, C$_3$-C$_5$, C$_3$-C$_4$, C$_4$-C$_6$, C$_4$-C$_5$, and C$_5$-C$_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Additional examples include that the phrase "optionally substituted with 1-5 substituents" is specifically intended to individually disclose a chemical group that can include 0, 1, 2, 3, 4, 5, 0-5, 0-4, 0-3, 0-2, 0-1, 1-5, 1-4, 1-3, 1-2, 2-5, 2-4, 2-3, 3-5, 3-4, and 4-5 substituents.

Compounds described herein can contain an asymmetric atom (also referred as a chiral center) and some of the compounds can contain two or more asymmetric atoms or centers, which can thus give rise to optical isomers (enantiomers) and diastereomers (geometric isomers). The present teachings include such optical isomers and diastereomers, including their respective resolved enantiomerically or diastereomerically pure isomers (e.g., (+) or (−) stereoisomer) and their racemic mixtures, as well as other mixtures of the enantiomers and diastereomers. In some embodiments, optical isomers can be obtained in enantiomerically enriched or pure form by standard procedures known to those skilled in the art, which include, for example, chiral separation, diastereomeric salt or ester formation, kinetic resolution, enzymatic resolution, and asymmetric synthesis. The present teachings also encompass cis and trans isomers of compounds containing alkenyl moieties (e.g., alkenes and imines). It is also understood that the present teachings encompass all possible regioisomers in pure form and mixtures thereof, which can be obtained with standard separation procedures known to those skilled in the art, for examples, column chromatography, thin-layer chromatography, simulated moving-bed chromatography, and high-performance liquid chromatography. For example, perylene compounds of the present teachings can include any perylene derivatives in their pure form or mixtures thereof, where the perylene derivatives can be substituted with 1, 2, 3, 4, 5, 6, 7, or 8 substituents. Specifically, the perylene derivatives can include compounds having the moiety:

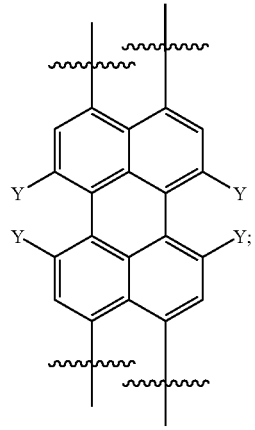

where Y, at each occurrence, can be H, an electron-withdrawing group, or a leaving group; where the electron-withdrawing group and the leaving group are as defined herein. In various embodiments, two of the Y groups can be H and the other two Y groups independently can be an electron-withdrawing group or a leaving group. Accordingly, in the embodiments where two of the Y groups are H and the other two independently are an electron-withdrawing group or a leaving group, compounds of the present teachings can have regioisomers having the formulae:

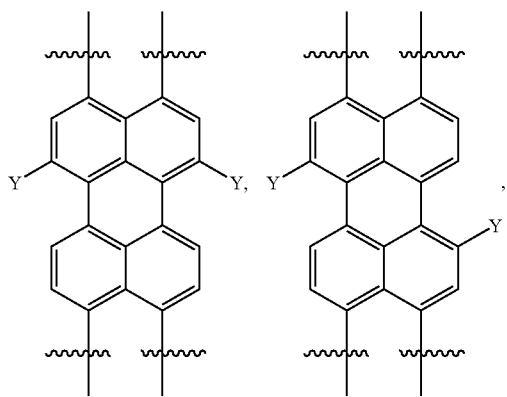

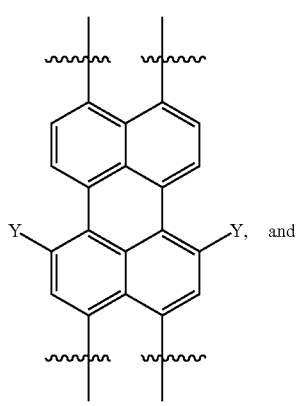

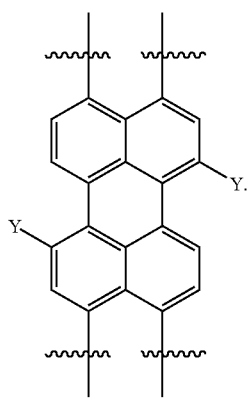

In certain embodiments, compounds of the present teachings can include compounds having formula i or ii:

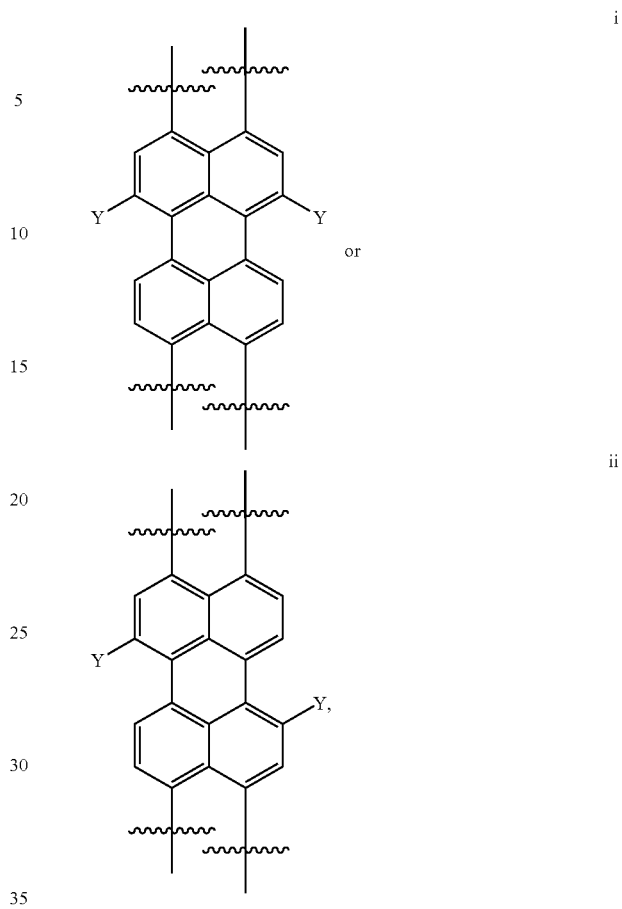

or mixtures thereof, where Y independently can be an electron-withdrawing group or a leaving group, for example, a halogen such as Br or a CN group. In particular embodiments, Y can be $R^3$, $R^4$, $R^5$, or $R^6$, where $R^3$, $R^4$, $R^5$, and $R^6$ are as defined herein. Further, it is specifically contemplated that the depiction of one regioisomer includes any other regioisomer and any regioisomeric mixtures unless specifically stated otherwise. Accordingly, the use of compounds of formula i include compounds of formula II (and vice versa) and mixtures of compounds of formulae i and ii.

The electron-donating or electron-withdrawing properties of the most common substituents, reflecting all common classes of substituents, have been determined, quantified, and published. The most common quantification of electron-donating and electron-withdrawing properties is in terms of Hammett σ values. Hydrogen has a Hammett σ value of zero, while other substituents have Hammett σ values that increase positively or negatively in direct relation to their electron-withdrawing or electron-donating characteristics. Substituents with negative Hammett σ values are considered electron-donating, while those with positive Hammett σ values are considered electron-withdrawing. See Lange's Handbook of Chemistry, 12th ed., McGraw Hill, 1979, Table 3-12, pp. 3-134 to 3-138, which lists Hammett σ values for a large number of commonly encountered substituents and is incorporated by reference herein. It should be understood that the term "electron-accepting group" can be used synonymously herein with "electron acceptor" and "electron-withdrawing group." In particular, an "electron-withdrawing group" ("EWG") or an "electron-accepting group" or an "electron-acceptor" refers to a functional group that draws electrons to itself more than a hydrogen atom would if it occupied the same position in a molecule. Examples of electron-withdrawing groups include, but are not limited to, halogens or halides (e.g., F, Cl, Br, I), —NO$_2$, —CN, —NC, —OH, —OR$^o$, —SH, —SR$^o$, —S(R$^o$)$_2$$^+$, —NH$_2$, —NHR$^o$, —NRO$_2$, —N(R$^o$)$_3$$^+$, —SO$_3$H, —SO$_2$R$^o$, —SO$_3$R$^o$, —SO$_2$NHR$^o$, —SO$_2$N(R$^o$)$_2$, —COOH, —COR$^o$, —COOR$^o$, —CONHR$^o$, —CON(R$^o$)$_2$, C$_{1-10}$ haloalkyl groups, C$_{6-14}$ aryl groups, and 5-14 membered heteroaryl groups; where R$^o$, at each occurrence, is a C$_{1-10}$ alkyl group, a C$_{2-10}$ alkenyl group, a C$_{2-40}$ alkynyl group, a C$_{1-10}$ haloalkyl group, a C$_{1-10}$ alkoxy group, a C$_{6-14}$ aryl group, a C$_{3-14}$ cycloalkyl group, a 3-14 membered cycloheteroalkyl group, or a 5-14 membered heteroaryl group.

As used herein, a "leaving group" ("LG") refers to a charged or uncharged atom (or group of atoms) that can be displaced as a stable species as a result of, for example, a substitution or elimination reaction. Examples of leaving groups include, but are not limited to, halide (e.g., Cl, Br, I), azide (N$_3$), thiocyanate (SCN), nitro (NO$_2$), cyanate (CN), water (H$_2$O), ammonia (NH$_3$), and sulfonate groups (e.g., OSO$_2$—R, wherein R can be a C$_{1-10}$ alkyl group or a C$_{6-44}$ aryl group each optionally substituted with 1-4 groups independently selected from a C$_{1-10}$ alkyl group and an electron-withdrawing group) such as tosylate (toluenesulfonate, OTs), mesylate (methanesulfonate, OMs), brosylate (p-bromobenzenesulfonate, OBs), nosylate (4-nitrobenzenesulfonate, ONs), and triflate (trifluoromethanesulfonate, OTf).

As used herein, a "p-type semiconducting material" or a "p-type semiconductor" refers to a semiconducting material having holes as the majority current carriers. In some embodiments, when a p-type semiconducting material is deposited on a substrate, it can provide a hole mobility in excess of about 10$^{-5}$ cm$^2$/Vs. In the case of field-effect devices, a p-type semiconductor can also exhibit a current on/off ratio of greater than about 10.

As used herein, a "n-type semiconducting material" or a "n-type semiconductor" refers to a semiconducting material having electrons as the majority current carriers. In some embodiments, when a n-type semiconducting material is deposited on a substrate, it can provide an electron mobility in excess of about 10$^{-5}$ cm$^2$/Vs. In the case of field-effect devices, an n-type semiconductor can also exhibit a current on/off ratio of greater than about 10.

As used herein, "field effect mobility" refers to a measure of the velocity with which charge carriers, for example, holes (or units of positive charge) in the case of a p-type semiconducting material and electrons in the case of an n-type semiconducting material, move through the material under the influence of an electric field.

As used herein, a compound can be considered "ambient stable" or "stable at ambient conditions" when the carrier mobility or the reduction-potential of the compound is maintained at about its initial measurement when the compound is exposed to ambient conditions, for example, air, ambient temperature, and humidity over a period of time. For example, a compound can be described as ambient stable if its carrier mobility or reduction potential does not vary more than 20% or more than 10% from its initial value after exposure to ambient conditions, i.e., air, humidity and temperature, over a 3 day, 5 day, or 10 day period.

As used herein, "solution-processable" refers to compounds, materials, or compositions that can be used in various solution-phase processes including spin-coating, printing (e.g., inkjet printing, screen printing, pad printing, gravure printing, flexographic printing, offset printing, microcontact printing, and lithographic printing), spraying, electrospray coating, drop casting, zone-casting, dip coating, and blade coating.

At various places in the present application temperatures are disclosed in ranges. It is specifically intended that the description includes narrower ranges of temperatures within such ranges, as well as the maximum and minimum temperatures embracing such range of temperatures.

Throughout the specification, structures may or may not be presented with chemical names. Where any question arises as to nomenclature, the structure prevails.

In one aspect, the present teachings provide compounds having formula I:

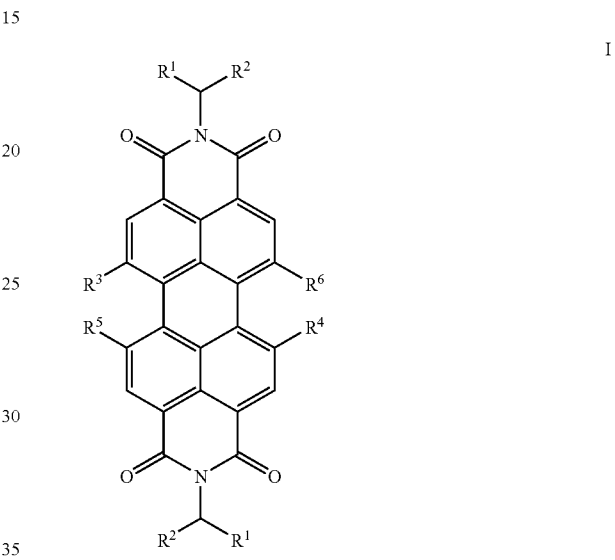

wherein:

R$^1$ and R$^2$, at each occurrence, independently are selected from H, a C$_{1-30}$ alkyl group, a C$_{2-30}$ alkenyl group, a C$_{2-30}$ alkynyl group, a C$_{1-30}$ haloalkyl group, and a 3-22 membered cyclic moiety, wherein each of the C$_{1-30}$ alkyl group, the C$_{2-30}$ alkenyl group, the C$_{2-30}$ alkynyl group, the C$_{1-30}$ haloalkyl group, and the 3-22 membered cyclic moiety is optionally substituted with 1-4 groups independently selected from halogen, —CN, —NO$_2$, —C(O)H, —C(O)OH, —CONH$_2$, —OH, —NH$_2$, —CO(C$_{1-10}$ alkyl), —C(O)OC$_{1-10}$ alkyl, —CONH(C$_{1-10}$ alkyl), —CON(C$_{1-10}$ alkyl)$_2$, —S—C$_{1-10}$ alkyl, —O—(CH$_2$CH$_2$O)$_n$(C$_{1-10}$ alkyl), —NH(C$_{1-10}$ alkyl), —N(C$_{1-10}$ alkyl)$_2$, a C$_{1-10}$ alkyl group, a C$_{2-10}$ alkenyl group, a C$_{2-10}$ alkynyl group, a C$_{1-10}$ haloalkyl group, a C$_{1-10}$ alkoxy group, a C$_{6-14}$ aryl group, a C$_{3-14}$ cycloalkyl group, a 3-14 membered cycloheteroalkyl group, and a 5-14 membered heteroaryl group;

at least one of R$^1$ and one of R$^2$, both of which are attached to a common carbon atom, independently are selected from a C$_{1-30}$ alkyl group, a C$_{2-30}$ alkenyl group, a C$_{2-30}$ alkynyl group, a C$_{1-30}$ haloalkyl group, and a 3-22 membered cyclic moiety, each optionally substituted as described herein;

R$^3$, R$^4$, R$^5$, and R$^6$ independently are H or an electron-withdrawing group; and n is 1, 2, 3, or 4.

In some embodiments, R$^1$ and R$^2$, at each occurrence, independently can be selected from a C$_{1-30}$ alkyl group, a C$_{2-30}$ alkenyl group, a C$_{2-30}$ alkynyl group, a C$_{1-30}$ haloalkyl group, and a 3-22 membered cyclic moiety, each optionally substituted with 1-4 groups independently selected from halogen, —CN, —NO$_2$, —C(O)H, —C(O)OH, —CONH$_2$, —OH, —NH$_2$, —CO(C$_{1-10}$ alkyl), —C(O)OC$_{1-10}$ alkyl, —CONH(C$_{1-10}$ alkyl), —CON(C$_{1-10}$ alkyl)$_2$, —S—C$_{1-10}$ alkyl, —O—(CH$_2$CH$_2$O)$_n$(C$_{1-10}$ alkyl), —NH(C$_{1-10}$ alkyl), —N(C$_{1-10}$ alkyl)$_2$, a C$_{1-10}$ alkyl group, a C$_{2-10}$ alkenyl group, a C$_{2-10}$ alkynyl group, a C$_{1-10}$ haloalkyl group, a C$_{1-10}$ alkoxy group, a C$_{6-14}$ aryl group, a C$_{3-14}$ cycloalkyl group, a 3-14 membered cycloheteroalkyl group, and a 5-14 membered heteroaryl group, and n is as described herein. The 3-22 membered cyclic moiety can be selected from a C$_{6-22}$ aryl group, a 5-22 membered heteroaryl group, a C$_{3-22}$ cycloalkyl group, and a 3-22 membered cycloheteroalkyl group, each of which can be optionally substituted as described herein.

In certain embodiments, R$^1$ and R$^2$, at each occurrence, independently can be selected from a C$_{1-12}$ alkyl group, a C$_{1-12}$ haloalkyl group, and a 3-14 membered monocyclic moiety, each optionally substituted with 1-4 groups independently selected from halogen, —CN, —NO$_2$, —C(O)H, —C(O)OH, —CONH$_2$, —OH, —NH$_2$, —CO(C$_{1-10}$ alkyl), —C(O)OC$_{1-10}$ alkyl, —CONH(C$_{1-10}$ alkyl), —CON(C$_{1-10}$ alkyl)$_2$, —S—C$_{1-10}$ alkyl, —O—(CH$_2$CH$_2$O)$_n$(C$_{1-10}$ alkyl), —NH(C$_{1-10}$ alkyl), —N(C$_{1-10}$ alkyl)$_2$, a C$_{1-10}$ alkyl group, a C$_{2-10}$ alkenyl group, a C$_{2-10}$ alkynyl group, a C$_{1-40}$ haloalkyl group, a C$_{1-10}$ alkoxy group, a C$_{6-14}$ aryl group, a C$_{3-14}$ cycloalkyl group, a 3-14 membered cycloheteroalkyl group, and a 5-14 membered heteroaryl group, and n is 1, 2, or 3. In particular embodiments, R$^1$ and R$^2$, at each occurrence, independently can be selected from a C$_{1-42}$ alkyl group, a C$_{1-12}$ haloalkyl group, and a phenyl group optionally substituted with 1-4 groups independently selected from a halogen, a C$_{1-6}$ alkyl group, and a C$_{1-6}$ haloalkyl group. For example, R$^1$ and R$^2$, at each occurrence, can be selected from —CH$_3$, —C$_2$H$_5$, —C$_3$H$_7$, —C$_4$H$_9$, —C$_5$H$_{11}$, —C$_6$H$_{13}$, and a phenyl group optionally substituted with 1-4 halo groups or C$_{1-6}$ alkyl groups.

In various embodiments, R$^1$ and R$^2$ can be asymmetrical (i.e., the carbon atom to which both R$^1$ and R$^2$ are attached can be a chiral center). For example, R$^1$ and R$^2$ can differ in terms of length, type of chemical group, or substitution pattern. In some embodiments, R$^1$, at each occurrence, can be selected from a C$_{1-12}$ alkyl group, a C$_{1-12}$ haloalkyl group, and a phenyl group optionally substituted with 1-4 groups independently selected from a halogen, a C$_{1-6}$ alkyl group, and a C$_{1-6}$ haloalkyl group; while R$^2$, at each occurrence, can be different from R$^1$ and can be a C$_{1-6}$ alkyl group or a C$_{1-6}$ haloalkyl group. For example, R$^1$, at each occurrence, can be selected from —CH$_3$, —C$_2$H$_5$, —C$_4$H$_9$, —C$_5$H$_{11}$, —C$_6$H$_{13}$, and a phenyl group optionally substituted with 1-4 halo groups or C$_{1-6}$ alkyl groups; while R$^2$, at each occurrence, can be different from R$^1$ and can be selected from —CH$_3$, —CF$_3$, and —C$_2$H$_5$.

In various embodiments, at least one of R$^3$, R$^4$, R$^5$, and R$^6$ can be an electronic-withdrawing group. In some embodiments, R$^3$, R$^4$, R$^5$, and R$^6$ independently can be selected from H, halogen, —CN, —NO$_2$, —CF$_3$, —OCF$_3$, —CO$_2$(C$_{1-40}$ alkyl), —CONH(C$_{1-10}$ alkyl), —CON(C$_{1-10}$ alkyl)$_2$, —SO$_2$(C$_{1-40}$ alkyl), —SO$_3$(C$_{1-10}$ alkyl), —SO$_2$NH(C$_{1-10}$ alkyl), and —SO$_2$N(C$_{1-10}$ alkyl)$_2$. For example, each of R$^3$, R$^4$, R$^5$, and R$^6$ can be H, halogen, —CN, —NO$_2$, —CF$_3$, or —OCF$_3$.

In certain embodiments, at least one of R$^3$, R$^4$, R$^5$, and R$^6$ can be Br or —CN. For example, R$^3$ can be H, F, Cl, Br, I, or —CN; R$^4$ can be H, F, Cl, Br, I, or —CN; R$^5$ can be H, F, Cl, Br, I, or —CN; and R$^6$ can be H, F, Cl, Br, I, or —CN. In particular embodiments, each of R$^3$, R$^4$, R$^5$, and R$^6$ can be Br or —CN. For example, each of R$^3$ and R$^4$ can be Br or —CN; while each of R$^5$ and R$^6$ is H. In other embodiments, each of R$^3$ and R$^6$ can be Br or —CN; while each of R$^4$ and R$^5$ is H.

In various embodiments, compounds of the present teachings can have formula Ia or Ib:

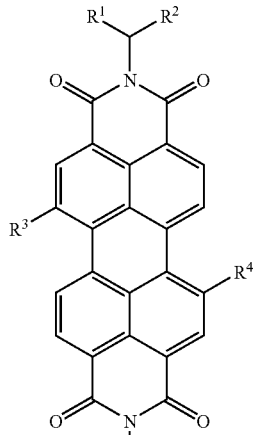

Ia

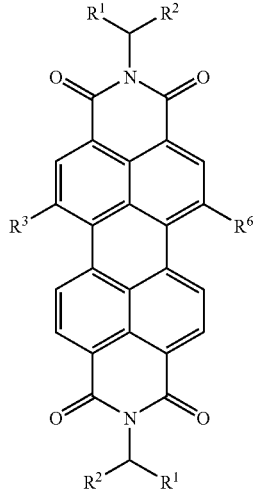

Ib wherein R$^1$, R$^2$, R$^3$, R$^4$, and R$^6$ are as defined herein.

Compounds of the present teachings can include, but are not limited to, the following compounds:

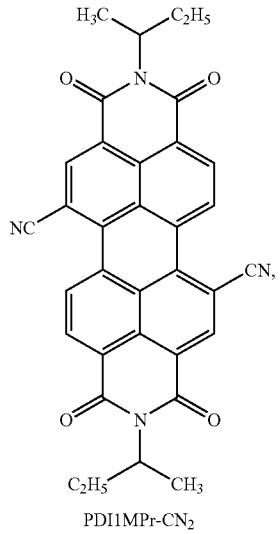

PDI1MPr-CN$_2$

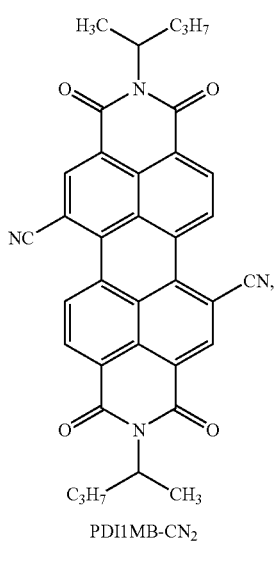
PDI1MB-CN$_2$
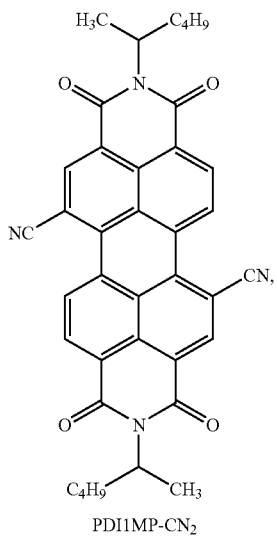
PDI1MP-CN$_2$
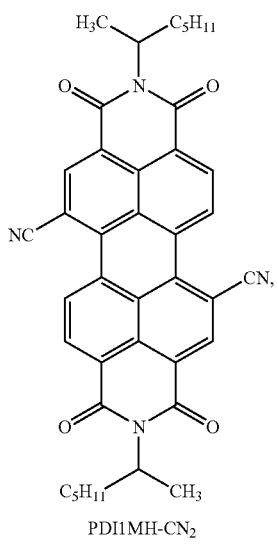
PDI1MH-CN$_2$
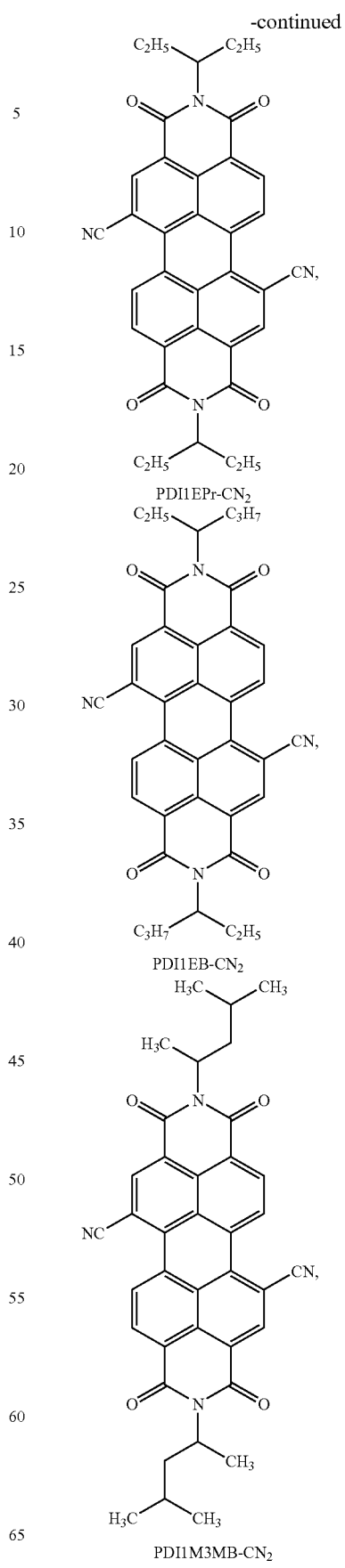
PDI1EPr-CN$_2$
PDI1EB-CN$_2$
PDI1M3MB-CN$_2$

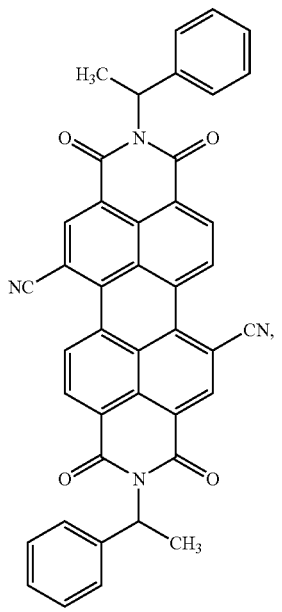
PDI1MPh-CN₂
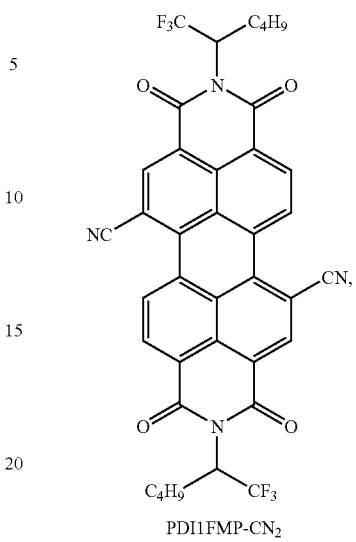
PDI1FMP-CN₂
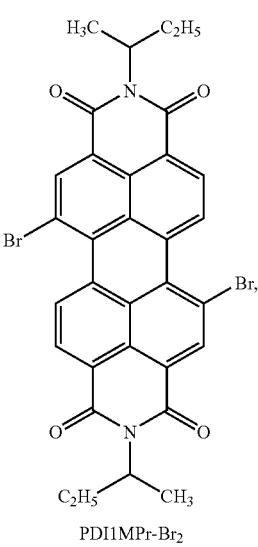
PDI1MPr-Br₂
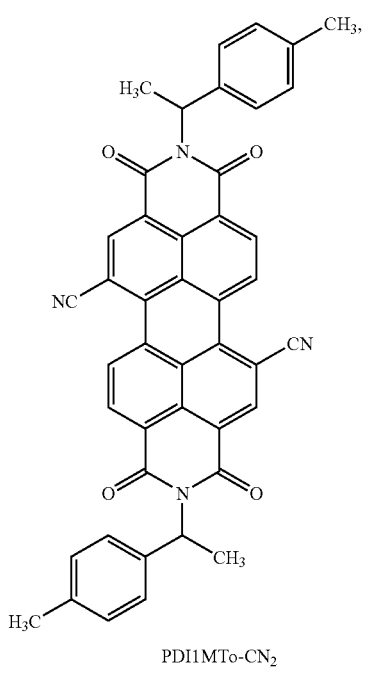
PDI1MTo-CN₂
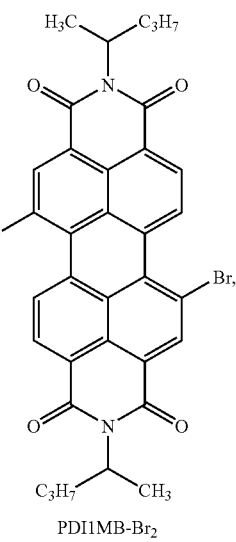
PDI1MB-Br₂

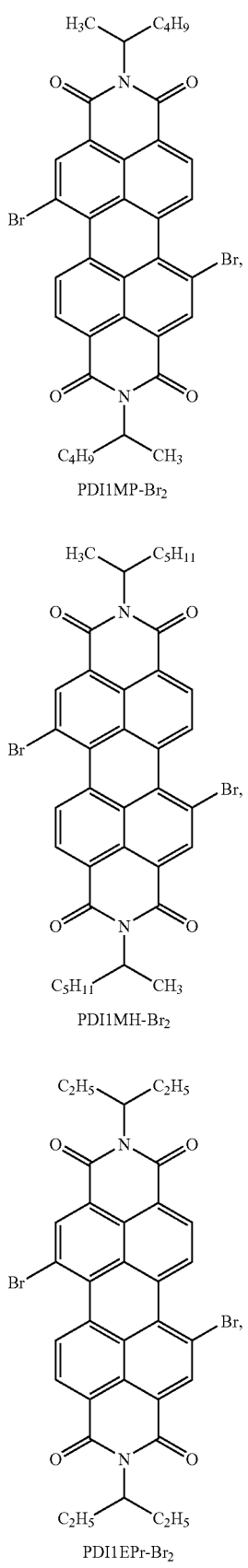
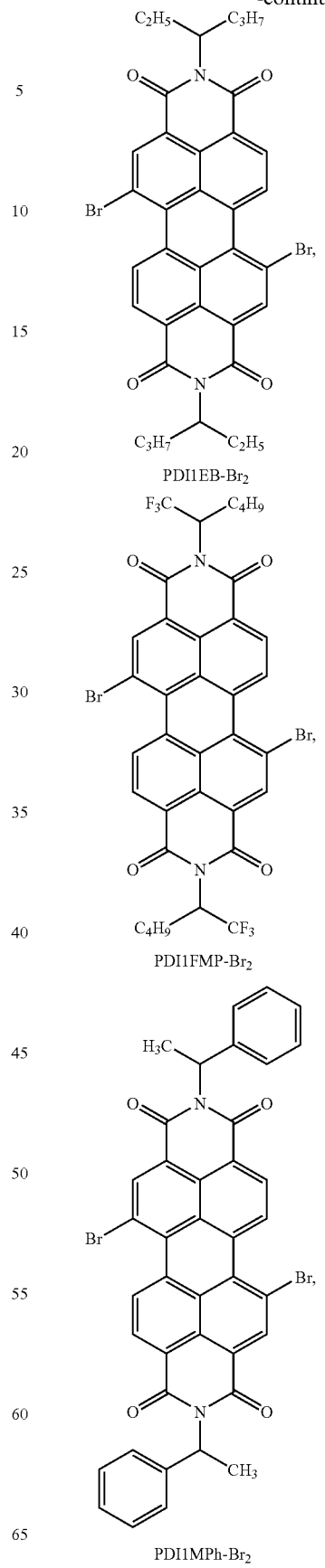

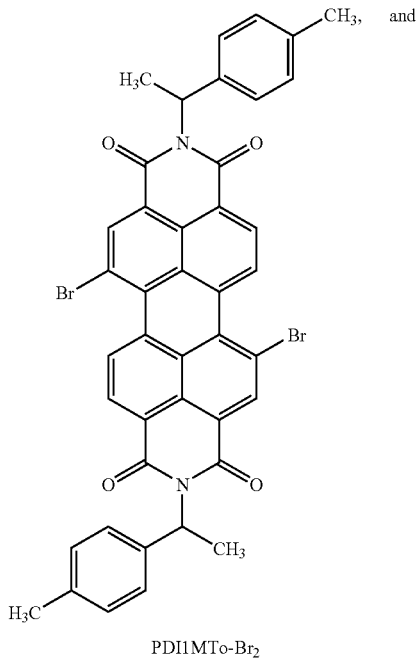

PDI1MTo-Br₂

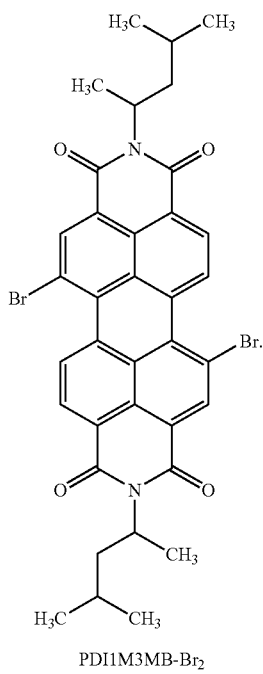 [SMILES: CC(C)CC(C)N1C(=O)c2ccc3c4c(Br)cc5c6c(ccc(c7c(Br)cc(c2c37)C1=O)c64)C(=O)N(C(C)CC(C)C)C5=O]

PDI1M3MB-Br₂

In another aspect, the present teachings provide methods of preparing compounds as disclosed herein. In various embodiments, the method can include reacting a compound of formula II:

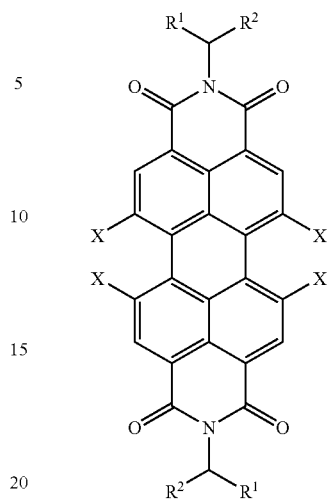

II with a cyanide;
wherein:
R¹ and R², at each occurrence, independently are selected from H, a $C_{1-30}$ alkyl group, a $C_{2-30}$ alkenyl group, a $C_{2-30}$ alkynyl group, a $C_{1-30}$ haloalkyl group, and a 3-22 membered cyclic moiety, wherein each of the $C_{1-30}$ alkyl group, the $C_{2-30}$ alkenyl group, the $C_{2-30}$ alkynyl group, the $C_{1-30}$ haloalkyl group, and the 3-22 membered cyclic moiety is optionally substituted with 1-4 groups independently selected from halogen, —CN, —NO₂, —C(O)H, —C(O)OH, —CONH₂, —OH, —NH₂, —CO($C_{1-10}$ alkyl), —C(O)O$C_{1-10}$ alkyl, —CONH($C_{1-10}$ alkyl), —CON($C_{1-10}$ alkyl)₂, —S—$C_{1-10}$ alkyl, —O—(CH₂CH₂O)ₙ($C_{1-10}$ alkyl), —NH($C_{1-10}$ alkyl), —N($C_{1-10}$ alkyl)₂, a $C_{1-10}$ alkyl group, a $C_{2-10}$ alkenyl group, a $C_{2-10}$ alkynyl group, a $C_{1-10}$ haloalkyl group, a $C_{1-10}$ alkoxy group, a $C_{6-14}$ aryl group, a $C_{3-14}$ cycloalkyl group, a 3-14 membered cycloheteroalkyl group, and a 5-14 membered heteroaryl group;
X, at each occurrence, is H or a leaving group;
n is 1, 2, 3, or 4.

In various embodiments, at least one of R¹ and at least one of R², both of which are attached to a common carbon atom, independently can be selected from a $C_{1-30}$ alkyl group, a $C_{2-30}$ alkenyl group, a $C_{2-30}$ alkynyl group, a $C_{1-30}$ haloalkyl group, and a 3-22 membered cyclic moiety, each of which can be optionally substituted with 1-4 groups independently selected from halogen, —CN, —NO₂, —C(O)H, —C(O)OH, —CONH₂, —OH, —NH₂, —CO($C_{1-10}$ alkyl), —C(O)O$C_{1-10}$ alkyl, —CONH($C_{1-10}$ alkyl), —CON($C_{1-10}$ alkyl)₂, —S—$C_{1-10}$ alkyl, —O—(CH₂CH₂O)ₙ($C_{1-10}$ alkyl), —NH($C_{1-10}$ alkyl), —N($C_{1-10}$ alkyl)₂, a $C_{1-10}$ alkyl group, a $C_{2-10}$ alkenyl group, a $C_{2-10}$ alkynyl group, a $C_{1-10}$ haloalkyl group, a $C_{1-10}$ alkoxy group, a $C_{6-14}$ aryl group, a $C_{3-14}$ cycloalkyl group, a 3-14 membered cycloheteroalkyl group, and a 5-14 membered heteroaryl group.

In some embodiments, the cyanide can be LiCN, NaCN, KCN, CuCN, AgCN, or trimethylsilyl cyanide (TMSCN). In certain embodiments, the cyanide can be CuCN or AgCN. In particular embodiments, the cyanide can be CuCN.

In some embodiments, the reaction can be conducted at room temperature, for example, between about 20° C. and about 30° C. In some embodiments, the reaction can be conducted at a temperature that is different from room temperature. For example, the temperature can be lower or higher than room temperature. In certain embodiments, the reaction can be conducted at an elevated temperature, i.e., a temperature higher than room temperature. For example, the elevated temperature can be between about 50° C. and about 300° C. In particular embodiments, the elevated temperature can be between about 50° C. and about 180° C., for example, between about 70° C. and about 150° C. (e.g., about 70° C. or about 150° C.).

In various embodiments, compound of formula II can be prepared by reacting a compound of formula III:

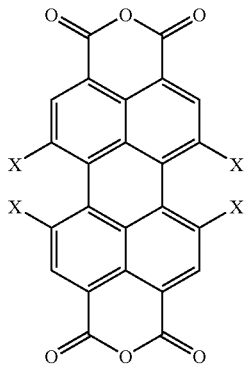

III with an amine in an aprotic solvent, wherein X is as defined herein.

In various embodiments, the amine can have the formula

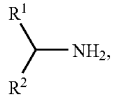

where $R^1$ and $R^2$ are as defined herein. In some embodiments, the amine can be selected from a propylamine, a butylamine, a pentylamine, a hexylamine, a heptylamine, and an octylamine. Examples of the amine include sec-butylamine, 1-methylbutylamine, 1-methylpentylamine, 1-methylhexylamine, 1-ethylpropylamine, 1-ethylbutylamine, and 1,3-dimethylbutylamine.

In various embodiments, the aprotic solvent can include a ether. In some embodiments, the aprotic solvent can include $(C_{1-6} \text{ alkyl})O(CH_2CH_2O)_m(C_{1-6} \text{ alkyl})$, where m can be 1, 2, 3, 4, 5, or 6. In particular embodiments, the aprotic solvent can be a solvent or a solvent mixture that includes triethylene glycol dimethyl ether. For example, the aprotic solvent can be triethylene glycol dimethyl ether.

In various embodiments, the reaction can be conducted at room temperature. In various embodiments, the reaction can be conducted at a temperature that is different from room temperature. For example, the temperature can be lower or higher than room temperature. In certain embodiments, the reaction can be conducted at an elevated temperature, i.e., a temperature higher than room temperature. For example, the elevated temperature can be between about 50° C. and about 300° C. In particular embodiments, the elevated temperature can be between about 50° C. and about 200° C., for example, between about 70° C. and about 180° C. (e.g., about 165° C.).

In various embodiments, X, at each occurrence, can be H or halogen. For example, X, at each occurrence, can be H, F, Cl, Br, or I. In certain embodiments, X, at each occurrence, can be H or Br.

Compounds of formula II can include, but are not limited to, the following compounds:

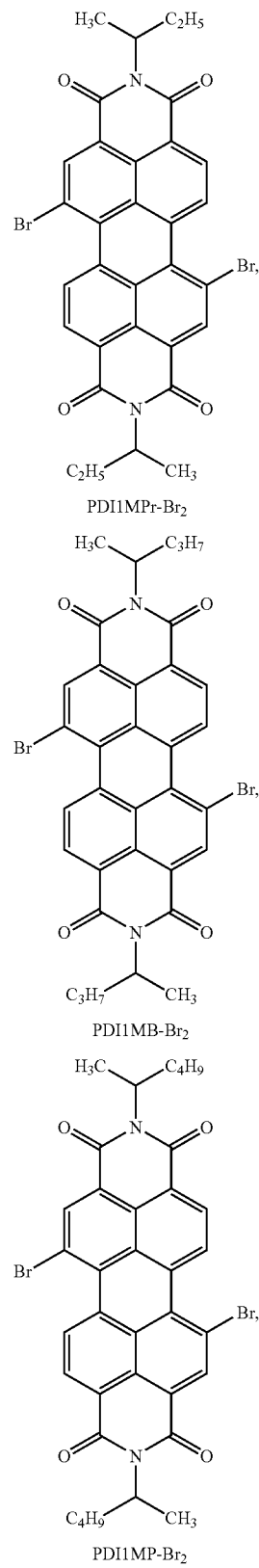

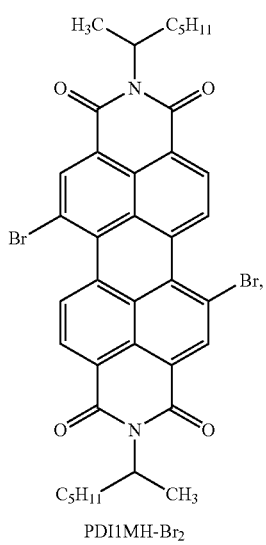
PDI1MH-Br$_2$
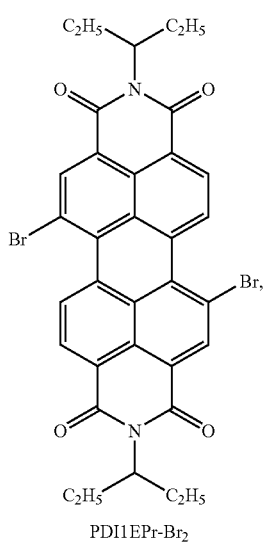
PDI1EPr-Br$_2$
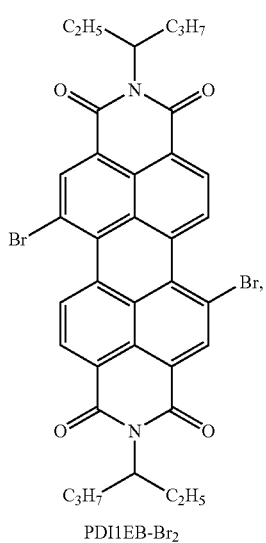
PDI1EB-Br$_2$
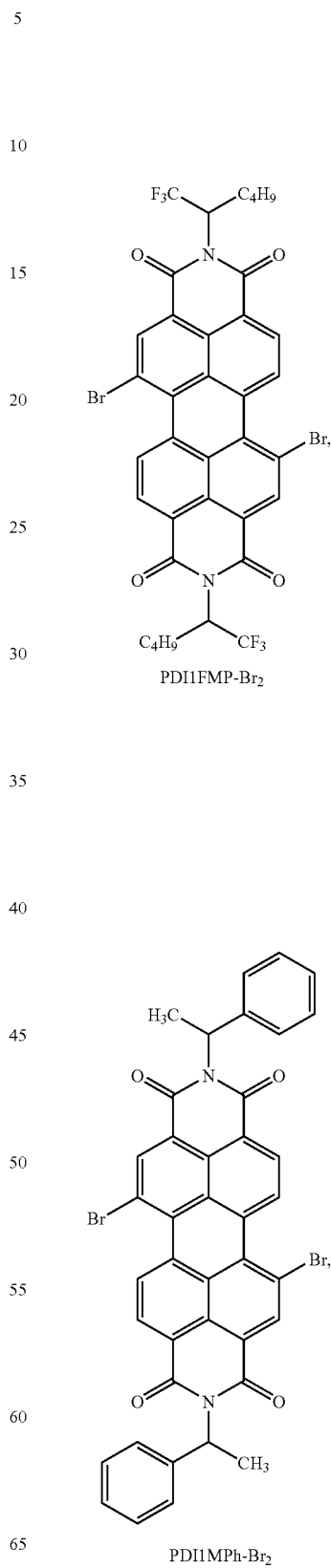
PDI1FMP-Br$_2$
PDI1MPh-Br$_2$

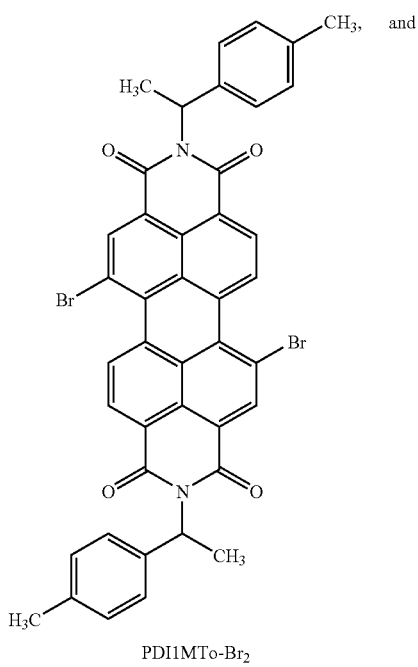

PDI1MTo-Br$_2$

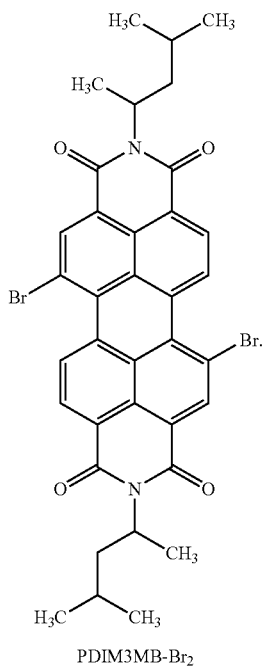 [SMILES: CC(C)CC(C)N1C(=O)c2ccc3c4c(Br)cc5c6c(ccc(c7c(Br)cc(c2c37)C1=O)c64)C(=O)N(C(C)CC(C)C)C5=O]

PDIM3MB-Br$_2$

Compounds of the present teachings can be prepared in accordance with the procedures outlined in Scheme 1 below, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (NMR, e.g., $^1$H or $^{13}$C), infrared spectroscopy (IR), spectrophotometry (e.g., UV-visible), mass spectrometry (MS), or by chromatography such as high pressure liquid chromatography (HPLC), gas chromatography (GC), gel-permeation chromatography (GPC), or thin layer chromatography (TLC).

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

Scheme 1

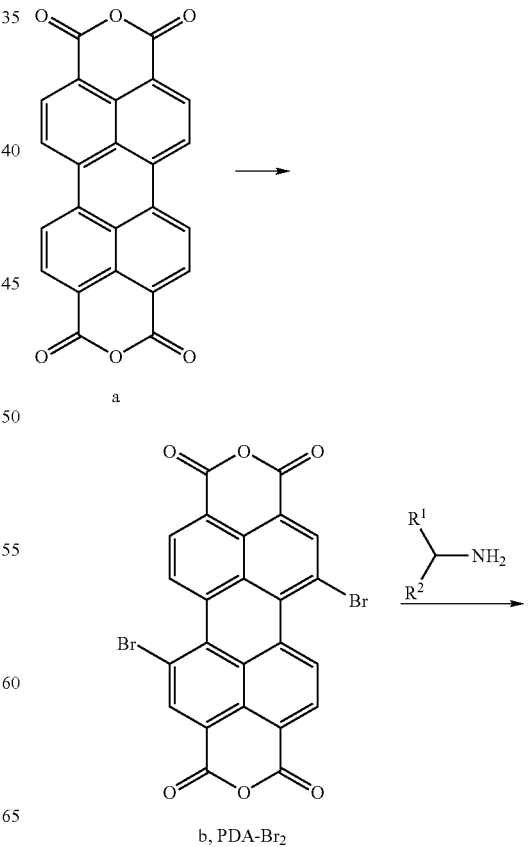

a b, PDA-Br$_2$

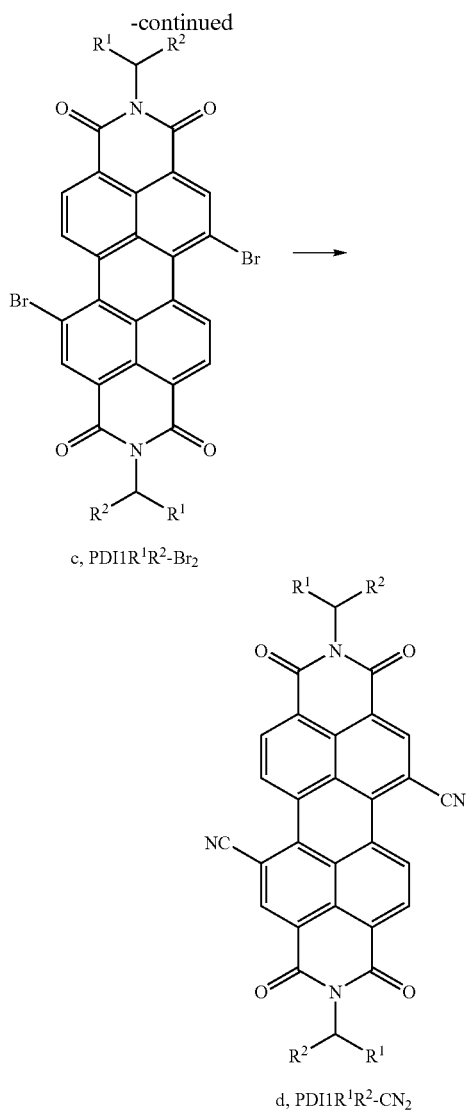

c, PDI1R¹R²-Br₂ d, PDI1R¹R²-CN₂

As shown in Scheme 1, perylene-3,4:9,10-tetracarboxylic acid dianhydride, a, can be brominated at 1,7-positions to provide PDA-Br₂, b, which upon reacting with a primary amine can provide a bis(dicarboximide), c. The substitution of the bromo groups in c by cyano groups can produce a dicyano-substituted bis(dicarboximide), d. Although not shown in Scheme 1, the bromination of a can also produce regioisomers of b, for example, 1,6-dibromo-perylene-3,4:9, 10-tetracarboxylic acid dianhydride, subsequently resulting in regioisomers of d, for example, 1,6-dicyano bis(dicarboximide).

Compounds of formula I can be used to prepare semiconductor materials (e.g., compositions and composites), which in turn can be used to fabricate various articles of manufacture, structures, and devices. In some embodiments, semiconductor materials incorporating one or more compounds of the present teachings can exhibit n-type semiconducting activity.

As certain embodiments of the compounds disclosed herein can be soluble in common solvents, the present teachings can offer processing advantages in fabricating electrical devices such as thin film semiconductors, field-effect devices, organic light emitting diodes (OLEDs), organic photovoltaics, photodetectors, capacitors, and sensors. As used herein, a compound can be considered soluble in a solvent when at least 1 mg of the compound can be dissolved in 1 mL of the solvent. Examples of common organic solvents include petroleum ethers; acetonitrile; aromatic hydrocarbons such as benzene, toluene, xylene, and mesitylene; ketones such as acetone and methyl ethyl ketone; ethers such as tetrahydrofuran, dioxane, bis(2-methoxyethyl)ether, diethyl ether, diisopropyl ether, and t-butyl methyl ether; alcohols such as methanol, ethanol, butanol, and isopropyl alcohol; aliphatic hydrocarbons such as hexanes; acetates such as methyl acetate, ethyl acetate, methyl formate, ethyl formate, isopropyl acetate, and butyl acetate; amides such as dimethylformamide and dimethylacetamide; sulfoxides such as dimethylsulfoxide; halogenated aliphatic and aromatic hydrocarbons such as dichloromethane, chloroform, ethylene chloride, chlorobenzene, dichlorobenzene, and trichlorobenzene; and cyclic solvents such as cyclopentanone, cyclohexanone, and 2-methypyrrolidone. Examples of common inorganic solvents include water and ionic liquids.

Accordingly, the present teachings further provide compositions that include one or more compounds disclosed herein dissolved or dispersed in a liquid medium, for example, an organic solvent, an inorganic solvent, or combinations thereof (e.g., a mixture of organic solvents, inorganic solvents, or organic and inorganic solvents). In some embodiments, the composition can further include one or more additives independently selected from detergents, dispersants, binding agents, compatiblizing agents, curing agents, initiators, humectants, antifoaming agents, wetting agents, pH modifiers, biocides, and bactereriostats. For example, surfactants and/or other polymers (e.g., polystyrene, polyethylene, poly-alpha-methylstyrene, polyisobutene, polypropylene, polymethylmethacrylate, and the like) can be included as a dispersant, a binding agent, a compatiblizing agent, and/or an antifoaming agent. In some embodiments, such compositions can include one or more compounds disclosed herein, for example, two or more different compounds of the present teachings can be dissolved in an organic solvent to prepare a composition for deposition. In certain embodiments, the composition can include two or more regioisomers, for example, compounds having the formulae Ia and Ib. Further, it should be understood that the devices described herein also can comprise one or more compounds of the present teachings, for example, two or more regioisomers as described herein. In particular embodiments, the composition can include two or more regioisomers having the formulae Ia and Ib.

Various deposition techniques, including various solution-processing techniques, have been used in preparing organic electronics. For example, much of the printed electronics technology has focused on inkjet printing, primarily because this technique offers greater control over feature position and multilayer registration. Inkjet printing is a noncontact process, which offers the benefits of not requiring a preformed master (compared to contact printing techniques), as well as digital control of ink ejection, thereby providing drop-on-demand printing. Micro dispensing is another non-contact method of printing. However, contact printing techniques have the key advantage of being well-suited for very fast roll-to-roll processing. Exemplary contact printing techniques include, but are not limited to, screen-printing, gravure printing, offset printing, flexographic printing, lithographic printing, pad printing, and microcontact printing. As used herein, "printing" includes a noncontact process, for example, inkjet printing, micro dispensing, and the like, and a contact process, for example, screen-printing, gravure printing, offset printing, flexographic printing, lithographic printing, pad printing, microcontact printing, and the like. Other solution processing techniques include, for example, spin coating, drop-casting, zone casting, dip coating, blade coating, or spraying. In addition, the deposition step can be carried out by vacuum vapor-deposition.

The present teachings, therefore, further provide methods of preparing a semiconductor material. The methods can include preparing a composition that includes one or more compounds disclosed herein dissolved or dispersed in a liquid medium such as a solvent or a mixture of solvents, and depositing the composition on a substrate to provide a semiconductor material (e.g., a thin film semiconductor) that includes one or more compounds disclosed herein. In various embodiments, the liquid medium can be an organic solvent, an inorganic solvent such as water, or combinations thereof. In some embodiments, the composition can further include one or more additives independently selected from viscosity modulators, detergents, dispersants, binding agents, compatiblizing agents, curing agents, initiators, humectants, antifoaming agents, wetting agents, pH modifiers, biocides, and bacteriostats. For example, surfactants and/or polymers (e.g., polystyrene, polyethylene, poly-alpha-methylstyrene, polyisobutene, polypropylene, polymethylmethacrylate, and the like) can be included as a dispersant, a binding agent, a compatiblizing agent, and/or an antifoaming agent. In some embodiments, the depositing step can be carried out by printing, including inkjet printing and various contact printing techniques (e.g., screen-printing, gravure printing, offset printing, pad printing, lithographic printing, flexographic printing, and microcontact printing). In other embodiments, the depositing step can be carried out by spin coating, drop-casting, zone casting, dip coating, blade coating, or spraying.

Various articles of manufacture including electronic devices, optical devices, and optoelectronic devices such as field effect transistors (e.g., thin film transistors), photovoltaics, organic light emitting diodes (OLEDs), complementary metal oxide semiconductors (CMOSs), complementary inverters, D flip-flops, rectifiers, and ring oscillators, that make use of the compounds and the semiconductor materials disclosed herein also as well as methods of making the same are within the scope of the present teachings.

Accordingly, the present teachings provide articles of manufacture such as the various devices described herein that include a composite having a semiconductor material of the present teachings, a substrate component, and/or a dielectric component. The substrate component can be selected from materials including doped silicon, an indium tin oxide (ITO), ITO-coated glass, ITO-coated polyimide or other plastics, aluminum or other metals alone or coated on a polymer or other substrate, a doped polythiophene or other polymers, and the like. The dielectric component can be prepared from inorganic dielectric materials such as various oxides (e.g., $SiO_2$, $Al_2O_3$, $HfO_2$), organic dielectric materials such as various polymeric materials (e.g., polycarbonate, polyester, polystyrene, polyhaloethylene, polyacrylate), self-assembled superlattice/self-assembled nanodielectric (SAS/SAND) materials (e.g., described in Yoon, M-H. et al., *PNAS*, 102 (13): 4678-4682 (2005), the entire disclosure of which is incorporated by reference herein), and hybrid organic/inorganic dielectric materials (e.g., described in U.S. patent application Ser. No. 11/642,504, the entire disclosure of which is incorporated by reference herein). In some embodiments, the dielectric component can include the crosslinked polymer blends described in U.S. patent application Ser. Nos. 11/315,076, 60/816,952, and 60/861,308, the entire disclosure of each of which is incorporated by reference herein. The composite also can include one or more electrical contacts. Suitable materials for the source, drain, and gate electrodes include metals (e.g., Au, Al, Ni, Cu), transparent conducting oxides (e.g., ITO, IZO, ZITO, GZO, GIO, GITO), and conducting polymers (e.g., poly(3,4-ethylenedioxythiophene) poly(styrenesulfonate) (PEDOT:PSS), polyaniline (PANI), polypyrrole (PPy)). One or more of the composites described herein can be incorporated within various organic electronic, optical, and optoelectronic devices such as organic thin film transistors (OTFTs), specifically, organic field effect transistors (OFETs), as well as sensors, capacitors, unipolar circuits, complementary circuits (e.g., inverter circuits), and the like.

Figure 6:
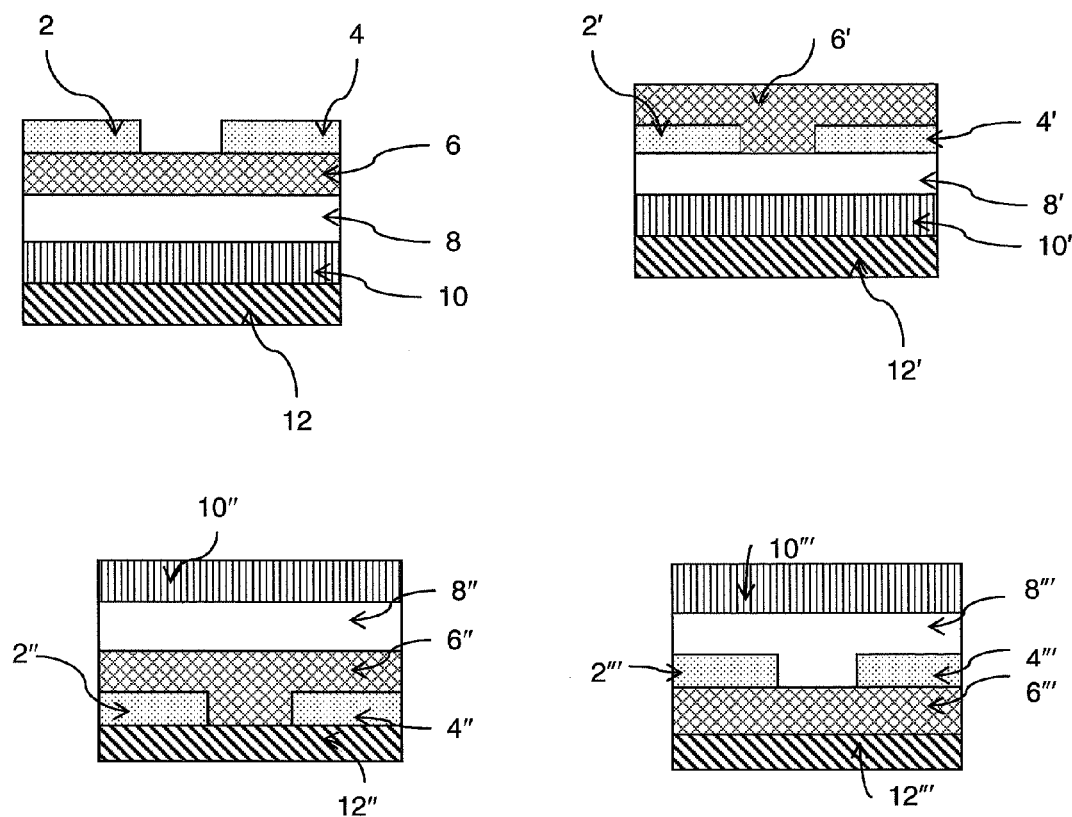
FIG. 6 illustrates different configurations of field effect transistors.

An aspect of the present teachings, therefore, relates to methods of fabricating an organic field effect transistor that incorporates a semiconductor material of the present teachings. The semiconductor materials of the present teachings can be used to fabricate various types of organic field effect transistors including top-gate top-contact capacitor structures, top-gate bottom-contact capacitor structures, bottom-gate top-contact capacitor structures, and bottom-gate bottom-contact capacitor structures. FIG. 6 illustrates the four common types of OFET structures: top-contact bottom-gate structure (top left), bottom-contact bottom-gate structure (top right), bottom-contact top-gate structure (bottom left), and top-contact top-gate structure (bottom right). As shown in FIG. 6, an OFET can include a dielectric layer (e.g., shown as 8, 8', 8", and 8'"), a semiconductor layer (e.g., shown as 6, 6', 6", and 6'"), a gate contact (e.g., shown as 10, 10', 10", and 10'"), a substrate (e.g., shown as 12, 12', 12", and 12'"), and source and drain contacts (e.g., shown as 2, 2', 2", 2'", 4, 4', 4", and 4'").

In certain embodiments, OTFT devices can be fabricated with the present compounds on doped silicon substrates, using $SiO_2$ as the dielectric, in top-contact geometries. In particular embodiments, the active semiconducting layer which incorporates at least a compound of the present teachings can be deposited by vacuum vapor deposition at room temperature or at an elevated temperature. In other embodiments, the active semiconducting layer which incorporates at least a compound of the present teachings can be applied by solution-based process, for example, spin-coating or jet printing. For top-contact devices, metallic contacts can be patterned on top of the films using shadow masks.

In certain embodiments, OTFT devices can be fabricated with the present compounds on plastic foils, using polymers as the dielectric, in top-gate bottom-contact geometries. In particular embodiments, the active semiconducting layer which incorporates at least a compound of the present teachings can be deposited at room temperature or at an elevated temperature. In other embodiments, the active semiconducting layer which incorporates at least a compound of the present teachings can be applied by spin-coating or printing as described herein. Gate and source/drain contacts can be made of Au, other metals, or conducting polymers and deposited by vapor-deposition and/or printing.

Other articles of manufacture in which compounds of the present teachings are useful are photovoltaics or solar cells. Compounds of the present teachings can exhibit broad optical absorption and/or a very positively shifted reduction potential making them desirable for such applications. Accordingly, the compounds described herein can be used as an n-type semiconductor in a photovoltaic design, which includes an adjacent p-type semiconducting material that forms a p-n junction. The compounds can be in the form of a thin film semiconductor, which can be a composite of the thin film semiconductor deposited on a substrate. Exploitation of compounds of the present teachings in such devices is within the knowledge of the skilled artisan.

Figure 7:
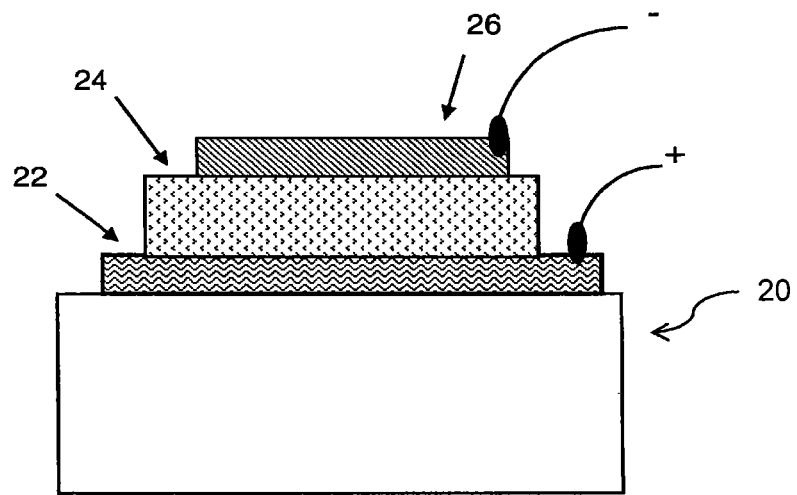
FIG. 7 illustrates a representative structure of a bulk-heterojunction organic photovoltaic device (also known as solar cell) which can incorporate one or more compounds of the present teachings as the donor and/or acceptor materials.

Accordingly, another aspect of the present teachings relates to methods of fabricating an organic light-emitting transistor, an organic light-emitting diode (OLED), or an organic photovoltaic device that incorporates one or more semiconductor materials of the present teachings. FIG. 7 illustrates a representative structure of a bulk-heterojunction organic photovoltaic device (also known as solar cell) which can incorporate one or more compounds of the present teachings as the donor and/or acceptor materials. As shown, a representative solar cell generally includes a substrate 20

Figure 8:
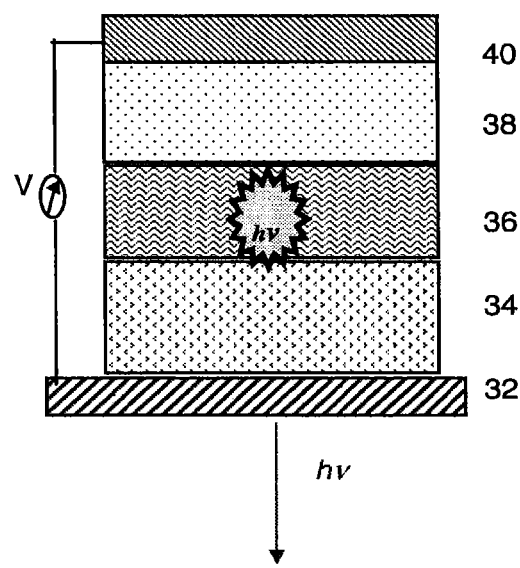
FIG. 8 illustrates a representative structure of an organic light-emitting device which can incorporate one or more compounds of the present teachings as electron-transporting and/or emissive and/or hole-transporting materials.

(e.g., glass), an anode 22 (e.g., ITO), a cathode 26 (e.g., aluminium or calcium), and an active layer 24 between the anode and the cathode which can incorporate one or more compounds of the present teachings as the electron donor (p-channel) and/or electron acceptor (n-channel) materials. FIG. 8 illustrates a representative structure of an OLED which can incorporate one or more compounds of the present teachings as electron-transporting and/or emissive and/or hole-transporting materials. As shown, an OLED generally includes a substrate 30 (not shown), a transparent anode 32 (e.g., ITO), a cathode 40 (e.g., metal), and one or more organic layers which can incorporate one or more compounds of the present teachings as hole-transporting (n-channel) (layer 34 as shown) and/or emissive (layer 36 as shown) and/or electron-transporting (p-channel) materials (layer 38 as shown).

The following examples are provided to illustrate further and to facilitate understanding of the present teachings and are not in any way intended to limit the invention.

Unless otherwise noted, all reagents were purchased from commercial sources and used without further purification. Some reagents were synthesized according to known procedures. Anhydrous tetrahydrofuran (THF) was distilled from sodium/benzophenone. Reactions were carried out under nitrogen unless otherwise noted. UV-Vis spectra were recorded on a Cary Model 1 UV-vis spectrophotometer. NMR spectra were recorded on a Varian Unity Plus 500 spectrometer (1H, 500 MHz; $^{13}$C, 125 MHz). Electrospray mass spectrometry was performed on a Thermo Finnegan model LCQ Advantage mass spectrometer.

Example 1

Preparation of Organic Semiconductors

A. Preparation of N,N'-bis(1-methylpentyl)-1,7-dicyanoperylene-3,4:9,10-bis(dicarboximide) (PDI1MP-CN$_2$)

Preparation of N,N'-bis(1-methylpentyl)-1,7-dibromoperylene-3,4:9,10-bis(dicarboximide) (PDI1MP—Br$_2$, R$^1$=CH$_3$, R$^2$=C$_4$H$_9$). A mixture of PDA-Br$_2$ (550 mg, 1.0 mmol) and 2-aminohexane (0.32 mL, 2.40 mmol) in triethylene glycol dimethyl ether (5 mL) was sealed under N$_2$ in a tube and stirred at 165° C. for 1 hour. After cooling to room temperature, the solvent was distilled to obtain 680 mg of a solid residue. The product was purified by column chromatography using CHCl$_3$ as the eluent to afford 400 mg (0.56 mmol, yield 55.8%) of a bright red solid. Elemental Analysis (calc. C, 60.35; H, 4.50; N, 3.91): C, 60.29; H, 4.54; N, 3.91.

Preparation of PDI1MP-CN$_2$ (R$^1$=CH$_3$, R$^2$=C$_4$H$_9$). Under nitrogen, CuCN (0.92 g, 10.2 mmol) was added to a mixture of PDI1MP—Br$_2$ (400 mg, 0.56 mmol) and dimethylformamide (DMF, 20 mL). The mixture was heated to 150° C. and stirred for 1 hour. After the mixture was cooled to room temperature, a precipitate formed which was collected by filtration and washed several times with MeOH. The crude product (340 mg) was purified by column chromatography using CHCl$_3$ as the eluent to afford 262 mg of a red solid. This solid was purified by recrystallization from 5 mL of DMF to afford the pure product as a brown solid (230 mg, 0.38 mmol, 67.5% yield). Elemental Analysis (calc. C, 74.98; H, 5.30; N, 9.20): C, 75.02; H, 5.20; N, 9.25; Solubility (DCB, 70° C.): 41.8 mg/mL.

B. Preparation of N,N'-bis(1-methylbutyl)-1,7-dicyanoperylene-3,4:9,10-bis(dicarboximide) (PDI1MB-CN$_2$)

Preparation of N,N'-bis(1-methylbutyl)-1,7-dibromoperylene-3,4:9,10-bis(dicarboximide) (PDI1MB—Br$_2$, R$^1$=CH$_3$, R$^2$=C$_3$H$_7$). A mixture of PDA-Br$_2$ (2.20 g, 4.0 mmol) and 2-aminopentane (1.12 mL, 9.60 mmol) in triethylene glycol dimethyl ether (20 mL) was stirred at 165° C. for 1 hour. After cooling to room temperature, MeOH (10 mL) was added, and the precipitate was collected by filtration and was purified by column chromatography using CHCl$_3$ as the eluent to afford the pure product as a red solid (220 mg, 0.32 mmol, yield 8%).

$^1$H NMR (CDCl$_3$, 500 MHz): δ 9.50 (d, 2H, J=8.0 Hz), 8.92 (s, 2H), 8.70 (d, 2H, J=8.0 Hz), 5.33-5.29 (m, 2H), 2.26-2.20 (m, 2H), 1.92-1.85 (m, 2H), 1.61 (d, 6H, J=6.5 Hz), 1.40-1.28 (m, 6H), 0.94 (t, 6H, J=7.5 Hz). Elemental Analysis (calc. C, 59.32; H, 4.10; N, 4.07): C, 59.44; H, 4.14; N, 4.11.

Preparation of PDI1MB-CN$_2$ (R$^1$=CH$_3$, R$^2$=C$_3$H$_7$). Under nitrogen, CuCN (480 mg, 5.3 mmol) was added to a suspension of PDI1MB—Br$_2$ (200 mg, 0.29 mmol) in DMF (10.5 mL). This mixture was heated to 150° C. and stirred for 13 hours. After cooling to room temperature, a precipitate formed which was collected by filtration and washed several times with MeOH. The crude brown solid (150 mg) was purified by column chromatography using CHCl$_3$ as the eluent to afford 40 mg of red solid (0.07 mmol, yield 24%). Elemental Analysis (calc. C, 74.47; H, 4.86; N, 9.65): C, 65.88; H, 4.33; N, 8.37.

C. Preparation of N,N'-bis(1-methylpropyl)-1,7-dicyanoperylene-3,4:9,10-bis(dicarboximide) (PDI1MPr—CN$_2$)

Preparation of N,N'-bis(1-methylpropyl)-1,7-dibromoperylene-3,4:9,10-bis(dicarboximide) (PDI1MPr—Br$_2$, R$^1$=CH$_3$, R$^2$=C$_2$H$_5$). A mixture of PDA-Br$_2$ (550 mg, 1.0 mmol) and sec-butylamine (0.24 mL, 2.40 mmol) in triethylene glycol dimethyl ether (5 mL) was sealed under N$_2$ in a j-young tube and stirred at 165° C. for 1 hour. After cooling to room temperature, MeOH (3 mL) was added and the solid was collected by filtration. The product was purified by column chromatography using CHCl$_3$ as the eluent to afford a red solid (60 mg, yield 10%).

$^1$H NMR (CDCl$_3$, 500 MHz): δ 9.50 (d, 2H, J=8.0 Hz), 8.92 (s, 2H), 8.70 (d, 2H, J=8.0 Hz), 5.24-5.19 (m, 2H), 2.27-2.21 (m, 2H), 2.00-1.95 (m, 2H), 1.61 (d, 6H, J=6.5 Hz), 0.94 (t, 6H, J=7.2 Hz). Elemental Analysis (calc. C, 58.20; H, 3.66; N, 4.24): C, 58.33; H, 3.68; N, 4.22.

Preparation of PDI1MPr—CN$_2$ (R$^1$=CH$_3$, R$^2$=C$_2$H$_5$). Under nitrogen, CuCN (501 mg, 5.5 mmol) was added to a suspension of PDI1MPr$_2$—Br$_2$ (200 mg, 0.30 mmol) in DMF (11 mL). The mixture was heated to 150° C. and stirred for 40 minutes. After cooling to room temperature, the solid was collected by filtration and washed several times with MeOH. The crude brown solid (169 mg) was purified by column chromatography using CHCl$_3$ as the eluent to afford 139 mg of a red solid (0.25 mmol, yield 84%). Elemental Analysis (calc. C, 73.90; H, 4.38; N, 10.14): C, 73.87; H, 4.46; N, 10.00.

D. Preparation of N,N'-bis(1-methylhexyl)-1,7-dicyanoperylene-3,4:9,10-bis(dicarboximide) (PDI1MH-CN$_2$)

Preparation of N,N'-bis(1-methylhexyl)-1,7-dibromoperylene-3,4:9,10-bis(dicarboximide) (PDI1MH—Br$_2$, R$^1$=CH$_3$, R$^2$=C$_5$H$_{11}$). A mixture of PDA-Br$_2$ (1.10 g, 2.0 mmol) and 2-aminoheptane (0.72 mL, 4.80 mmol) in triethylene glycol dimethyl ether (10 mL) and propionic acid (1.1 mL) was stirred at 165° C. for 1 hour. After cooling to room temperature, MeOH (15 mL) was added and a precipitate formed which was collected by filtration. The solid (1.24 g) was purified by column chromatography using CHCl$_3$ as the eluent to afford the pure product as a deep brown solid (586 mg, 0.79 mmol, yield 39%).

$^1$H NMR (CDCl$_3$, 500 MHz): δ 9.50 (d, 2H, J=8.0 Hz), 8.91 (s, 2H), 8.69 (d, 2H, J=8.5 Hz), 5.31-5.26 (m, 2H), 2.26-2.18 (m, 2H), 1.94-1.87 (m, 2H), 1.60 (d, 6H, J=6.5 Hz), 1.40-1.20 (m, 12H), 0.86 (t, 6H, J=7.0 Hz). Elemental Analysis (calc. C, 61.30; H, 4.87; N, 3.76): C, 61.45; H, 4.92; N, 3.89.

Preparation of PDI1MH-CN$_2$ (R$^1$=CH$_3$, R$^2$=C$_5$H$_{11}$). CuCN (131 mg, 1.46 mmol) was added to a mixture of PDI1MH—Br$_2$ (372 mg, 0.50 mmol) and DMF (5.6 mL) The mixture was stirred at 150° C. for 1 hour. After cooling to room temperature, the precipitate was filtered and washed several times with MeOH. The crude brown solid (312 mg) was purified by column chromatography using CHCl$_3$ as the eluent to afford 213 mg of red solid (0.33 mmol, yield 67%).

$^1$H NMR (CDCl$_3$, 500 MHz): δ 9.70 (d, 2H, J=8.0 Hz), 8.96 (s, 2H), 8.91 (d, 2H, J=8.0 Hz), 5.31-5.26 (m, 2H), 2.25-2.17 (m, 2H), 1.96-1.89 (m, 2H), 1.61 (d, 6H, J=7.0 Hz), 1.40-1.20 (m, 12H), 0.86 (t, 6H, J=7.0 Hz). Elemental Analysis (calc. C, 75.45; H, 5.70; N, 8.80): C, 75.49; H, 5.65; N, 8.90.

E. Preparation of N,N'-bis(1-ethylbutyl)-1,7-dicyanoperylene-3,4:9,10-bis(dicarboximide) (PDI1EB-CN$_2$)

Preparation of N,N'-bis(1-ethylbutyl)-1,7-dibromoperylene-3,4:9,10-bis(dicarboximide) (PDI1EB—Br$_2$, R$^1$=C$_2$H$_5$, R$^2$=C$_3$H$_7$). A mixture of PDA-Br$_2$ (1.1 g, 2.0 mmol) and 3-aminohexane (486 mg, 4.80 mmol) in triethylene glycol dimethyl ether (10 mL) and propionic acid (1.1 mL) was stirred at 165° C. for 1 hour. After cooling to room temperature, MeOH (15 mL) was added and the resulting precipitate collected by filtration. The solid was purified by column chromatography using CHCl$_3$ as the eluent to afford the pure product as a red solid (383 mg, 0.53 mmol, yield 26.7%). Elemental Analysis (calc. C, 60.35; H, 4.50; N, 3.91): C, 60.57; H, 4.54; N, 4.05.

Preparation of PDI1EB-CN$_2$ (R$^1$=C$_2$H$_5$, R$^2$=C$_3$H$_7$). Under nitrogen, CuCN (105 mg, 1.17 mmol) was added to a mixture of PDI1EB—Br$_2$ (243 mg, 0.40 mmol) and DMF (4.5 mL). The mixture was heated to 150° C. and stirred for 1 hour. After cooling to room temperature, a solid formed which was collected by filtration and washed several times with MeOH. The crude product (223 mg) was purified by column chromatography using CHCl$_3$ as eluent to afford the pure product as a deep red solid (150 mg, 0.25 mmol, yield 62%). Elemental Analysis (calc. C, 74.98; H, 5.30; N, 9.20): C, 72.92; H, 5.30; N, 8.97.

F. Preparation of N,N'-bis(1-ethylpropyl)-1,7-dicyanoperylene-3,4:9,10-bis(dicarboximide) (PDI1EPr—CN$_2$)

Preparation of N,N'-bis(1-ethylpropyl)-1,7-dibromoperylene-3,4:9,10-bis(dicarboximide) (PDI1EPr—Br$_2$, R$^1$=C$_2$H$_5$, R$^2$=C$_2$H$_5$). A mixture of PDA-Br$_2$ (2.20 g, 4.0 mmol) and 3-aminopentane (1.12 mL, 9.60 mmol) in triethylene glycol dimethyl ether (15 mL) and propionic acid (2.2 mL) was stirred at 165° C. for 1 hour. After cooling to room temperature, MeOH (25 mL) was added and the precipitate was collected by filtration. The resulting solid was purified by column chromatography using CHCl$_3$ as the eluent to afford a red solid (1.11 g, 1.61 mmol, yield 40.3%). Elemental Analysis (calc. C, 59.32; H, 4.10; N, 4.07): C, 59.04; H, 4.07; N, 4.06.

Preparation of PDI1EPr—CN$_2$ (R$^1$=C$_2$H$_5$, R$^2$=C$_2$H$_5$). Under nitrogen, CuCN (321 mg, 3.57 mmol) was added to a mixture of PDI1EPr—Br$_2$ (826 mg, 1.20 mmol) and DMF (13.7 mL). The resulting mixture was heated at 150° C. for 1 hour. After cooling to room temperature, the precipitate was collected by filtration and washed several times with MeOH. The crude solid (772 mg) was purified by column chromatography to afford the pure product as a red solid (511 mg, 0.88 mmol, yield 47.5%). Elemental Analysis (calc. C, 74.47; H, 4.86; N, 9.65): C, 74.37; H, 4.93; N, 9.62.

G. Preparation of N,N'-bis(1,3-dimethylbutyl)-1,7-dicyanoperylene-3,4:9,10-bis(dicarboximide) (PDI1M3MB-CN$_2$)

Preparation of N,N'-bis(1,3-dimethylbutyl)-1,7-dibromoperylene-3,4:9,10-bis(dicarboximide) (PDI1M3MB—Br$_2$, R$^1$=CH3, R$^2$=2-methylpropyl). A mixture of PDA-Br$_2$ (2.20 mg, 41.0 mmol) and 1,3-dimethylbutylamine (1.35 mL, 9.60 mmol) in triethylene glycol dimethyl ether (15 mL) was sealed under N$_2$ in a tube and stirred at 165° C. for 1 hour. After cooling to room temperature, MeOH (25 mL) was added and the precipitate was collected by filtration. The crude product was purified by column chromatography (CHCl$_3$) to afford PDI1M3MB—Br$_2$ as a red solid (1.10 g, 1.54 mmol, yield 39%).

M.p.>340° C.; $^1$H NMR (CDCl$_3$, 500 MHz): δ 9.48 (d, 2H, J=8.0 Hz), 8.91 (s, 2H), 8.67 (d, 2H, J=8.5 Hz), 5.41-5.36 (m, 2H), 2.26-2.20 (m, 2H), 1.74-1.68 (m, 2H), 1.59 (d, 6H, J=6.5 Hz), 1.56-1.46 (m, 2H), 0.97-0.93 (m, 12H). Elemental Analysis (calc. C, 60.35; H, 4.50; N, 3.91): C, 60.35; H, 4.53; N, 3.91.

Preparation of N,N'-bis(1,3-dimethylbutyl)-1,7-dicyano-3,4:9,10-bis(dicarboximide) (PDI1M3MB-CN$_2$, R$^1$=CH$_3$, R$^2$=2-methypropyl). Under nitrogen, CuCN (401 mg, 4.46 mmol) was added to a mixture of PDI1M3MB—Br$_2$ (913 mg, 1.50 mmol) and DMF (17.1 ml). The mixture was heated to 150° C. and stirred for 1 hour, cooled, and filtered. The solid was washed with MeOH several times and was purified by column chromatography (CHCl$_3$) to give 284 mg of a red solid, which was further purified by recrystallization from 7 mL DMF to afford PDI1M3MB-CN$_2$ as a brown solid (264 mg, 0.43 mmol, yield 29%).

M.p.>340° C.; $^1$H NMR (CDCl$_3$, 500 MHz): δ 9.69 (d, 2H, J=8.5 Hz), 8.96 (s, 2H), 8.91 (d, 2H, J=8.0 Hz), 5.41-5.36 (m, 2H), 2.24-2.18 (m, 2H), 1.76-1.71 (m, 2H), 1.60 (d, 6H, J=7.0 Hz), 1.54-1.48 (m, 2H), 0.97-0.94 (m, 12H). Elemental Analysis (calc. C, 74.98; H, 5.30; N, 9.20): C, 75.04; H, 5.31; N, 9.16. Solubility (DCB, 70° C.): 37.1 mg/mL.

Example 2

Cyclic Voltammetry

Cyclic voltammetry experiments were conducted using an Epsilon single-channel potentiometer and a BAS C3 cell stand (a one-compartment cell with a C disk working electrode, a bare Ag reference electrode, and a Pt wire counter electrode). Appropriate precautions were taken to eliminate water and oxygen during measurement. All measurements were performed under N$_2$ by dissolving the compound (1-3 mg) in a 0.1 M THF/TBAPF$_6$ solutions with scanning rates between 60-150 mV/s. When the voltammograms are (quasi)

reversible, it is possible to extract formal potentials ($E^{1/2}$) as the midpoints between peak potentials for the forward and reverse scans.

Table 1 summarizes certain physical and electrical properties of some compounds of the present teachings, including $E_{red}$ values obtained from the cyclic voltammetry experiments. N,N'-Bis(4-n-octyl)-1,7-dicyanoperylene-3,4:9,10-bis(dicarboximide) (PDI8-CN$_2$), N,N'-bis[(3S)-3,7-dimethyl-6-octenyl]-1,7-dicyanoperylene-3,4:9,10-bis(dicarboximide) (PDICitr-CN$_2$), N,N'-bis(2-ethylhexyl)-1,7-dicyanoperylene-3,4:9,10-bis(dicarboximide) (PDI2EH-CN$_2$), and N,N'-bis(2-methylhexyl)-1,7-dicyanoperylene-3,4:9,10-bis(dicarboximide) (PDI2MH-CN$_2$) were included as comparative representative compounds.

TABLE 1

| Compounds | M.p. (°C.) | $E_{red}$ (V) | Compound | M.p. (°C.) | $E_{red}$ (V) | Solubility (mg/mL) DCB | CHCl$_3$ |
|---|---|---|---|---|---|---|---|
| PDI8-Br$_2$ | 281-282 | -0.40 | PDI8-CN$_2$ | >303-305 | -0.150 | 4 | 4 |
| PDI2EH-Br$_2$ | 225-227 | -0.39 | PDI2EH-CN$_2$ | 319-321 | -0.130 | 5 | 5 |
| PDICitr-Br$_2$ | 206-208 | -0.40 | PDICitr-CN$_2$ | 278-280 | -0.142 | 8 | |
| PDI1MH-Br$_2$ | 267-269 | -0.38 | PDI1MH-CN$_2$ | 305-307 | -0.094 | 52 | 54 |
| PDI1MP-Br$_2$ | 290-292 | -0.41 | PDI1MP-CN$_2$ | >328 | -0.071 | 40 | 43 |
| PDI1MB-Br$_2$ | 316-318 | -0.39 | PDI1MB-CN$_2$ | >340 | -0.083 | 5 | |
| PDI1MPr-Br$_2$ | 334-336 | -0.40 | PDI1MPr-CN$_2$ | >340 | -0.091 | 8 | |
| PDI1EB-Br$_2$ | 319-321 | -0.34 | PDI1EB-CN$_2$ | >360 | -0.106 | 10 | 8 |
| PDI1EPr-Br$_2$ | 309-311 | -0.38 | PDI1EPr-CN$_2$ | >360 | -0.101 | 10 | |
| PDI2MH-Br$_2$ | 211-213 | -0.40 | PDI2MH-CN$_2$ | 284-286 | -0.120 | 5 | |
| PDI1M3MB-Br$_2$ | >340 | -0.39 | PDI1M3MB-CN$_2$ | >340 | -0.088 | 37 | 30 |

As shown in Table 1, compounds of the present teachings can exhibit solubilities as high as 50 mg/mL, for example, in cold organic solvents such as chloroform and dichlorobenzene. Greater solubilities (2-10 times) can be achieved using warm solvents. In particular, it should be noted that perylene compounds having imide nitrogens functionalized with 1-alkyl substituted alkyl groups (e.g., PDI1MH-CN$_2$, PDI1MP-CN$_2$, and PDI1M3MB-CN$_2$) showed an unexpected increase in solubility compared to similar compounds substituted with slightly different alkyl or alkenyl groups (i.e., PDI8-CN$_2$, PDI2EH-CN$_2$, PDICitr-CN$_2$, and PDI2MH-CN$_2$).

Example 3

FET Device Fabrication and Measurements

Thin-film transistor (TFT) devices (25-200 μm channel lengths (L) and 1.0-4.0 mm channel widths (W)) were fabricated with compounds of the present teachings using the top-contact configuration. Semiconductors films prepared with compounds of the present teachings were vacuum vapor-deposited (2-4 Ås$^{-1}$, P≈10$^{-6}$ Torr) or spin coated on n-doped Si/SiO$_2$ (300 nm thick thermal oxide) substrates, which had been pretreated with hexamethyldisilazane. XRD plots of these semiconductor films show sharp reflections, suggesting high crystallinity. The gate region was accessed by an ohmic contact to the Si substrate, and Au source and drain contacts were evaporated through a shadow mask onto the semiconductor layer. All electrical measurements were performed in ambient atmosphere. Data reported below are average values measured from at least three devices tested at different locations on the semiconductor film.

To allow comparison with other organic FETs, mobilities (μ) were calculated by standard field effect transistor equations. In traditional metal-insulator-semiconductor FETs (MISFETs), there is typically a linear and saturated regime in the $I_{DS}$ vs $V_{DS}$ curves at different $V_G$ (where $I_{DS}$ is the source-drain saturation current, $V_{DS}$ is the potential between the source and drain, and $V_G$ is the gate voltage, see, e.g., FIGS. 13-17). At large $V_{DS}$, the current saturates and is given by:

$$(I_{DS})_{sat} = (WC_i/2L)\mu(V_G - V_t)^2 \qquad (1)$$

where L and W are the device channel length and width, respectively, $C_i$ is the capacitance of the oxide insulator (~1× 10$^{-8}$ F/cm$^2$ for ~300 nm SiO$_2$), and $V_t$ is the threshold voltage.

Mobilities (μ) were calculated in the saturation regime by rearranging equation (1):

$$\mu_{sat} = (2I_{DS}L)/[WC_i(V_G - V_t)^2] \qquad (2)$$

The threshold voltage ($V_t$) can be estimated as the x intercept of the linear section of the plot of $V_G$ versus $(I_{DS})^{1/2}$ (at $V_{SD}$=-100 V).

Table 2 summarizes electron mobilities and current on/off ratios of certain compounds of the present teachings and comparative representative compounds that were formed into thin layer semiconductors by vacuum-deposition, spin-coating, or drop-casting. In particular, it should be noted that perylene compounds having imide nitrogens functionalized with 1-alkyl substituted alkyl groups showed an unexpected increase in current $I_{on}$:$I_{off}$ ratio compared to similar compounds substituted with slightly different alkyl or alkenyl groups (i.e., PDI8-CN$_2$ and PDICitr-CN$_2$). Further, certain compounds of the present teachings demonstrated an unexpected higher electron mobility than similar known compounds such as PDI8-CN$_2$ and PDICitr-CN$_2$.

TABLE 2

| | Vapor Deposition | | Spin-Coating | |
|---|---|---|---|---|
| Compounds | Mobility (cm$^2$/Vs) | $I_{on}$:$I_{off}$ | Mobility (cm$^2$/Vs) | $I_{on}$:$I_{off}$ |
| PDI8—CN$_2$ | 0.01-0.2 | 10$^4$-10$^5$ | 10$^{-5}$-10$^{-3}$ | 10$^2$-10$^4$ |
| PDI2EH—CN$_2$ | 0.1-0.3 | 10$^7$-10$^8$ | 0.2-0.3 | 10$^6$-10$^7$ |
| PDICitr-CN$_2$ | 0.01-0.1 | 10$^3$-10$^5$ | 10$^{-4}$-10$^{-3}$ | 10$^1$-10$^2$ |
| PDI1MH—CN$_2$ | 0.1-0.4 | 10$^8$ | 0.07-0.2 | 10$^6$-10$^8$ |
| PDI1MP—CN$_2$ | 0.3-0.8 | 10$^8$ | 0.03-0.2 | 10$^5$-10$^8$ |
| PDI1MB—CN$_2$ | 0.8-2.0 | 10$^9$-10$^{10}$ | 0.03-0.1 | 10$^5$-10$^7$ |
| PDI1MPr—CN$_2$ | 0.2-0.8 | 10$^7$ | 0.02-0.1 | 10$^5$-10$^7$ |
| PDI1EB—CN$_2$ | 0.1-0.5 | 10$^8$ | 0.005-0.01 | 10$^5$ |
| PDI1EPr—CN$_2$ | 0.01-0.1 | 10$^7$ | 0.005-0.01 | 10$^5$ |
| PDI2MH—CN$_2$ | 0.1-0.3 | 10$^7$ | 0.01 | 10$^6$ |
| PDI1M3MB—CN$_2$ | 0.3-0.5 | 10$^7$ | 0.03-0.2 | 10$^7$ |

Representative transfer plots of TFT devices fabricated with compounds of the present teachings are shown in FIGS. 1-5.

The present teachings encompass embodiments in other specific forms without departing from the spirit or essential characteristics thereof. The foregoing embodiments are therefore to be considered in all respects illustrative rather than limiting on the present teachings described herein. The scope of the present teachings is thus indicated by the appended claims rather than by the foregoing description, and all changes that come within the meaning and range of equivalency of the claims are intended to be embraced therein.

What is claimed is:

1. A compound of formula I:

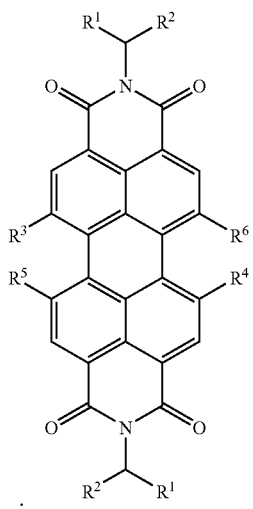

wherein:
- $R^1$ and $R^2$, at each occurrence, independently are selected from a $C_{1-30}$ alkyl group, a $C_{2-30}$ alkenyl group, a $C_{2-30}$ alkynyl group, a $C_{1-30}$ haloalkyl group, and a 3-22 membered cyclic moiety, each optionally substituted with 1-4 groups independently selected from halogen, —CN, —NO$_2$, —C(O)H, —C(O)OH, —CONH$_2$, —OH, —NH$_2$, —CO(C$_{1-10}$ alkyl), —C(O)OC$_{1-10}$ alkyl, —CONH(C$_{1-10}$ alkyl), —CON(C$_{1-10}$ alkyl)$_2$, —S—C$_{1-10}$ alkyl, —O—(CH$_2$CH$_2$O)$_n$(C$_{1-10}$ alkyl), —NH(C$_{1-10}$ alkyl), —N(C$_{1-10}$ alkyl)$_2$, a C$_{1-10}$ alkyl group, a C$_{2-10}$ alkenyl group, a C$_{2-10}$ alkynyl group, a C$_{1-10}$ haloalkyl group, a C$_{1-10}$ alkoxy group, a C$_{6-14}$ aryl group, a C$_{3-14}$ cycloalkyl group, a 3-14 membered cycloheteroalkyl group, and a 5-14 membered heteroaryl group;
- $R^3$, $R^4$, $R^5$, and $R^6$ independently are H or CN, wherein at least one of $R^3$, $R^4$, $R^5$, and $R^6$ is CN; and
- n is 1, 2, 3, or 4.

2. The compound of claim 1, wherein $R^1$ and $R^2$, at each occurrence, are selected from a $C_{1-12}$ alkyl group, a $C_{1-12}$ haloalkyl group, and a phenyl group optionally substituted with 1-4 groups independently selected from a halogen, a $C_{1-6}$ alkyl group, and a $C_{1-6}$ haloalkyl group.

3. The compound of claim 1, wherein $R^1$, at each occurrence, is selected from a $C_{1-12}$ alkyl group and a phenyl group optionally substituted with a $C_{1-6}$ alkyl group; and $R^2$, at each occurrence, is selected from a $C_{1-6}$ alkyl group and a $C_{1-6}$ haloalkyl group.

4. The compound of claim 1, wherein each of $R^1$ and $R^2$ is selected from —CH$_3$, —CF$_3$, —C$_2$H$_5$, —C$_3$H$_7$, —C$_4$H$_9$, —C$_5$H$_{11}$, and a phenyl group optionally substituted with a $C_{1-6}$ alkyl group.

5. The compound of claim 1, wherein each of $R^3$ and $R^4$ is —CN.

6. The compound of claim 1, wherein each of $R^3$ and $R^6$ is —CN.

7. The compound of claim 1, the compound having formula Ia or formula Ib:

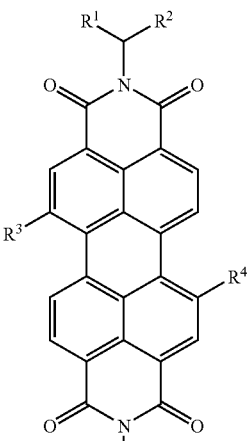

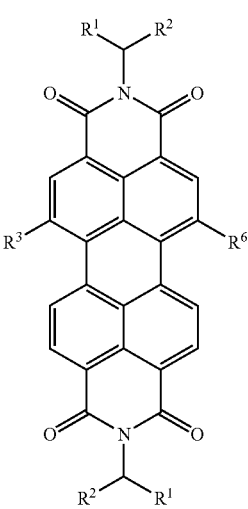

wherein $R^1$, $R^2$, $R^3$, $R^4$, and $R^6$ are as defined in claim 1.

8. The compound of claim 1, the compound having the formula:

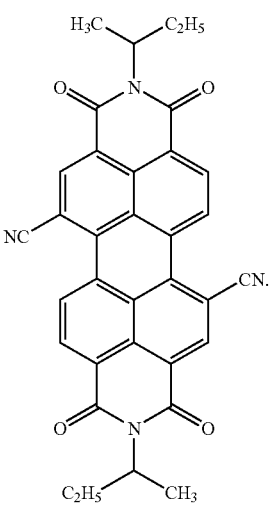

9. The compound of claim 1, the compound having the formula:
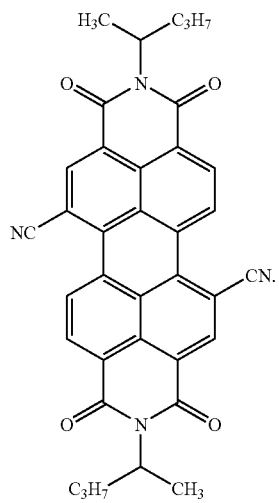
10. The compound of claim 1, the compound having the formula:
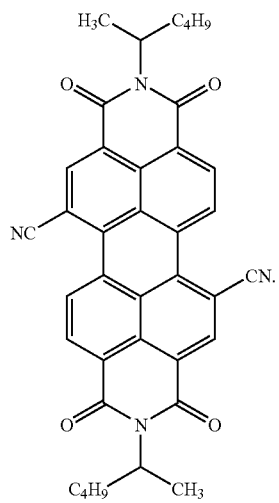
11. The compound of claim 1, the compound having the formula:
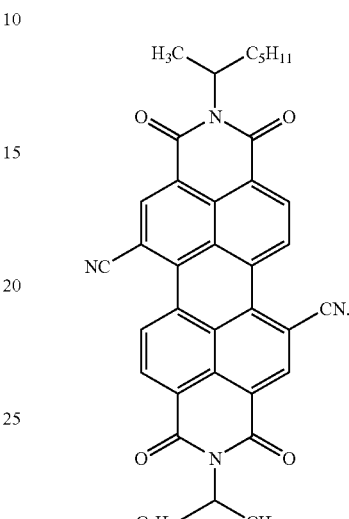
12. The compound of claim 1, the compound having the formula:
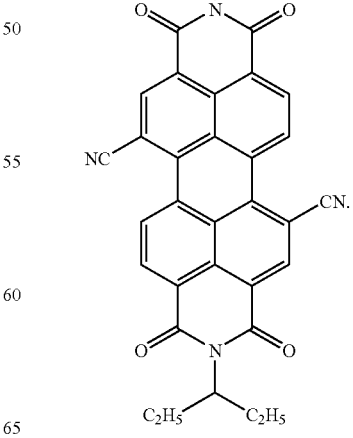

13. The compound of claim 1, the compound having the formula:
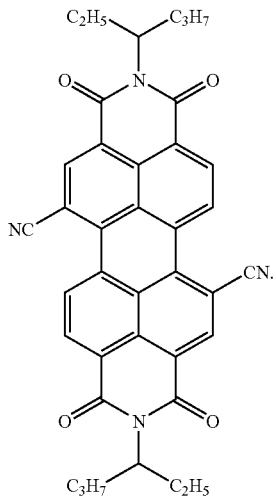
14. The compound of claim 1, the compound having the formula:
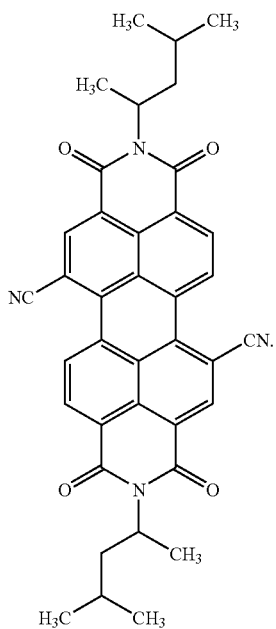
15. The compound of claim 1, the compound having the formula:
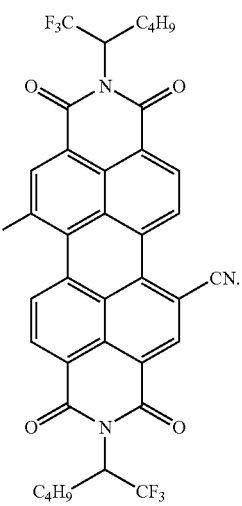
16. The compound of claim 1, the compound having the formula:
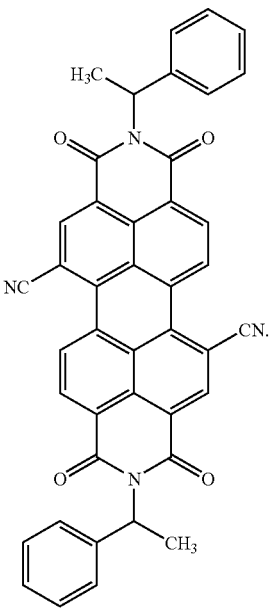

17. The compound of claim 1, the compound having the formula:

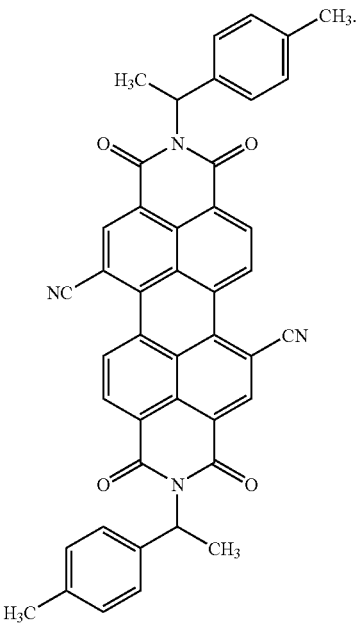

18. A method of making the compound of claim 1, said method comprising reacting a compound of formula II:

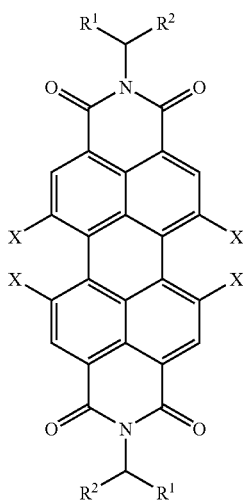

with a cyanide;
wherein
R$^1$ and R$^2$, at each occurrence, independently are selected from H, a C$_{1-30}$ alkyl group, a C$_{2-30}$ alkenyl group, a C$_{2-30}$ alkynyl group, a C$_{1-30}$ haloalkyl group, and a 3-22 membered cyclic moiety, each optionally substituted with 1-4 groups independently selected from halogen, —CN, —NO$_2$, —C(O)H, —C(O)OH, —CONH$_2$, —OH, —NH$_2$, —CO(C$_{1-10}$ alkyl), —C(O)OC$_{1-10}$ alkyl, —CONH(C$_{1-10}$ alkyl), —CON(C$_{1-10}$ alkyl)$_2$, —S—C$_{1-10}$ alkyl, —O—(CH$_2$CH$_2$O)$_n$(C$_{1-10}$ alkyl), —NH(C$_{1-10}$ alkyl), —N(C$_{1-10}$ alkyl)$_2$, a C$_{1-10}$ alkyl group, a C$_{2-10}$ alkenyl group, a C$_{2-10}$ alkynyl group, a C$_{1-10}$ haloalkyl group, a C$_{1-10}$ alkoxy group, a C$_{6-14}$ aryl group, a C$_{3-14}$ cycloalkyl group, a 3-14 membered cycloheteroalkyl group, and a 5-14 membered heteroaryl group;
at least one of R$^1$ and at least one of R$^2$, both of which are attached to a common carbon atom, are independently selected from a C$_{1-30}$ alkyl group, a C$_{2-30}$ alkenyl group, a C$_{2-30}$ alkynyl group, a C$_{1-30}$ haloalkyl group, and a 3-22 membered cyclic moiety, each optionally substituted as described herein;
X, at each occurrence, is H or a halogen; and
n is 1, 2, 3, or 4.

19. The method of claim 18, wherein the cyanide is CuCN.

20. The method of claim 18, wherein the reaction is conducted at an elevated temperature.

21. The method of claim 20, wherein the elevated temperature is about 70° C. or about 150° C.

22. The method of claim 18, wherein the compound of formula II is prepared by reacting a compound of formula III:

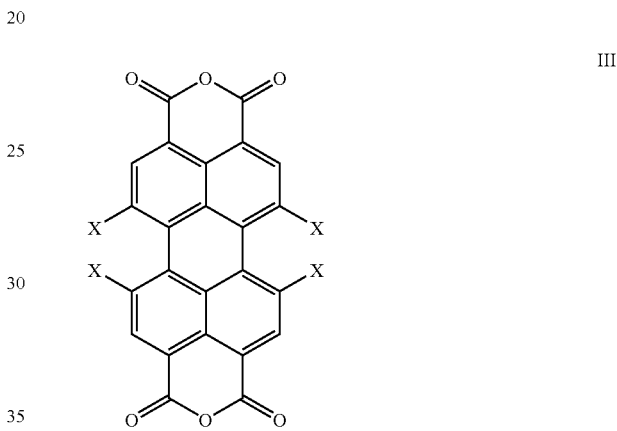

with an amine in an aprotic solvent, wherein X, at each occurrence, is H or a halogen.

23. The method of claim 22, wherein the amine is $$\begin{array}{c} R^1 \\ | \\ \text{—NH}_2, \\ | \\ R^2 \end{array}$$

wherein R$^1$ and R$^2$, at each occurrence, independently are selected from H, a C$_{1-30}$ alkyl group, a C$_{2-30}$ alkenyl group, a C$_{2-30}$ alkynyl group, a C$_{1-30}$ haloalkyl group, and a 3-22 membered cyclic moiety, each optionally substituted with 1-4 groups independently selected from halogen, —CN, —NO$_2$, —C(O)H, —C(O)OH, —CONH$_2$, —OH, —NH$_2$, —CO(C$_{1-10}$ alkyl), —C(O)OC$_{1-10}$ alkyl, —CONH(C$_{1-10}$ alkyl), —CON(C$_{1-10}$ alkyl)$_2$, —S—C$_{1-10}$ alkyl, —O—(CH$_2$CH$_2$O)$_n$(C$_{1-10}$ NH(C$_{1-10}$ alkyl), —N(C$_{1-10}$ alkyl)$_2$, a C$_{1-10}$ alkyl group, a C$_{2-10}$ alkenyl group, a C$_{2-10}$ alkynyl group, a C$_{1-10}$ haloalkyl group, a C$_{1-10}$ alkoxy group, a C$_{6-14}$ aryl group, a C$_{3-14}$ cycloalkyl group, a 3-14 membered cycloheteroalkyl group, and a 5-14 membered heteroaryl group; and n is 1, 2, 3, or 4.

24. The method of claim 22, wherein the aprotic solvent is (C$_{1-6}$ alkyl)O(CH$_2$CH$_2$O)$_m$(C$_{1-6}$ alkyl), and m is selected from 1, 2, 3, 4, 5, and 6.

25. The method of claim 22, wherein the aprotic solvent is triethylene glycol dimethyl ether.

26. The method of claim 18, wherein X, at each occurrence, is H or Br.

27. The method of claim 18, wherein the compound of formula II is selected from:
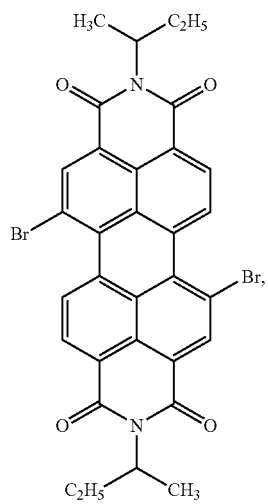
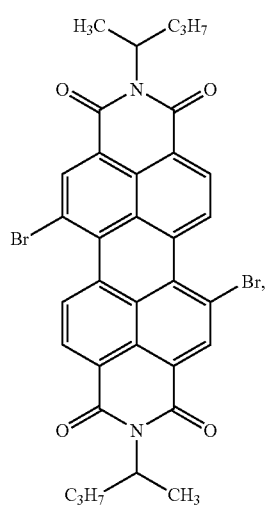
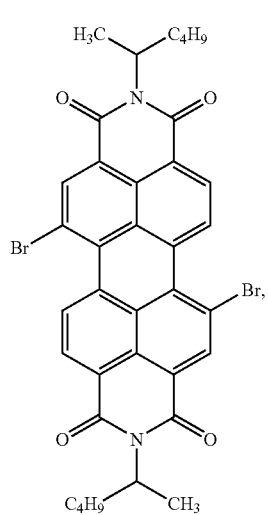
-continued
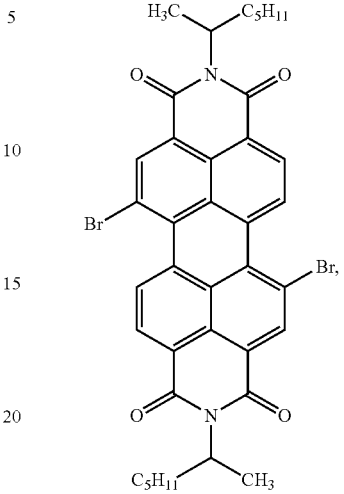

-continued

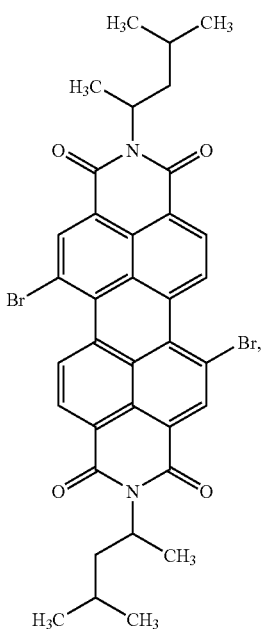

-continued

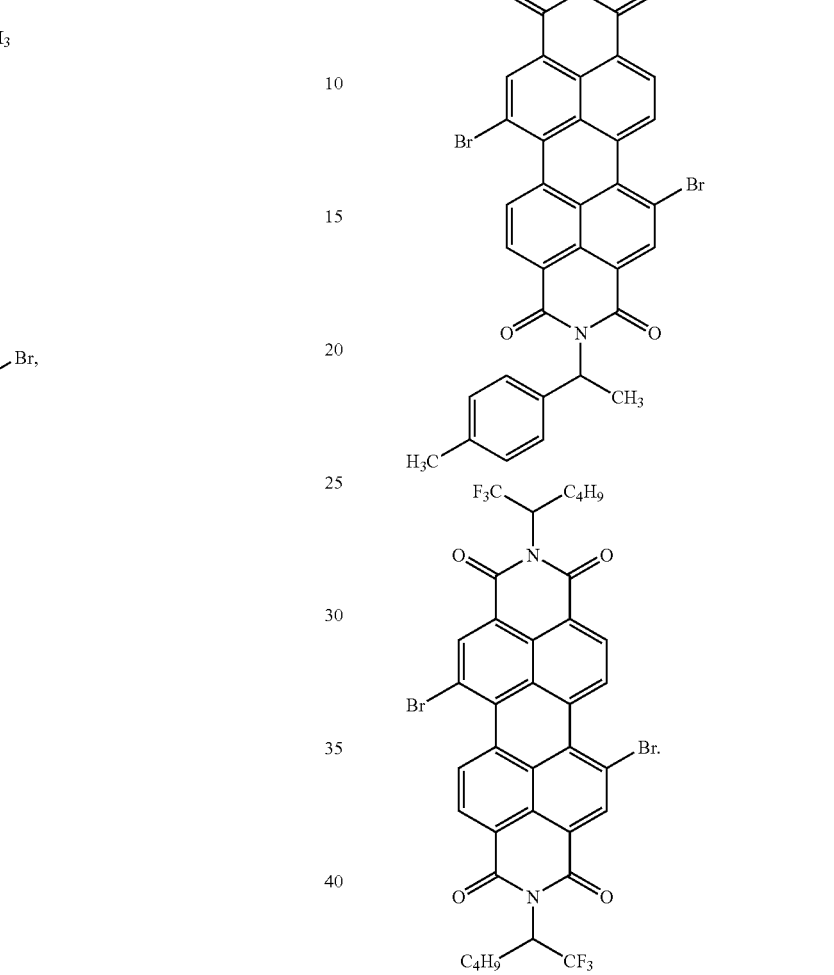

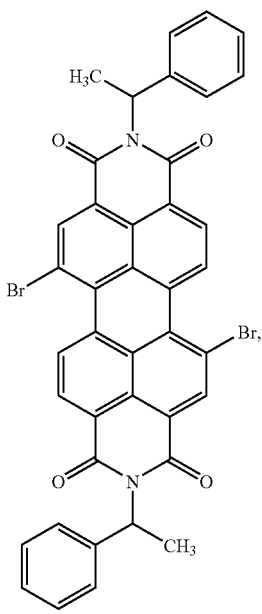

28. A composition comprising one or more compounds according to claim 1 dissolved or dispersed in a liquid medium.

29. The composition of claim 28, wherein the composition comprises two or more regioisomers of the one or more compounds according to claim 1.

30. The composition of claim 28, wherein the liquid medium is an organic solvent or a mixture of solvents.

31. An article of manufacture comprising one or more compounds according to claim 1.

32. The article of manufacture of claim 31, wherein the article of manufacture comprises two or more regioisomers of the compounds according to claim 1.

33. The article of manufacture of claim 31, wherein the article of manufacture is an electronic device, an optical device, or an optoelectronic device.

34. A thin film semiconductor comprising one or more compounds according to claim 1.

35. The thin film semiconductor of claim 34, wherein the thin film semiconductor comprises two or more regioisomers of a compound of formula I:

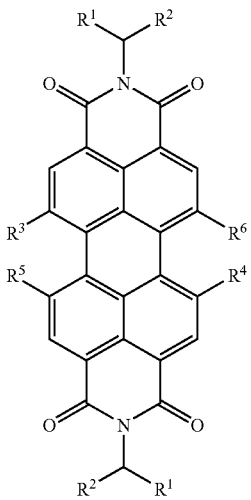

wherein:
R[1] and R[2], at each occurrence, independently are selected from a $C_{1-30}$ alkyl group, a $C_{2-30}$ alkenyl group, a $C_{2-30}$ alkynyl group, a $C_{1-30}$ haloalkyl group, and a 3-22 membered cyclic moiety, each optionally substituted with 1-4 groups independently selected from halogen, —CN, —NO$_2$, —C(O)H, —C(O)OH, —CONH$_2$, —OH, —NH$_2$, —CO(C$_{1-10}$ alkyl), —C(O)OC$_{1-10}$ alkyl, —CONH(C$_{1-10}$ alkyl), —CON(C$_{1-10}$ alkyl)$_2$, —S—C$_{1-10}$ alkyl, —O—(CH$_2$CH$_2$O)$_n$(C$_{1-10}$ alkyl), —NH(C$_{1-10}$ alkyl), —N(C$_{1-10}$ alkyl)$_2$, a C$_{1-10}$ alkyl group, a C$_{2-10}$ alkenyl group, a C$_{2-10}$ alkynyl group, a C$_{1-10}$ haloalkyl group, a C$_{1-10}$ alkoxy group, a C$_{6-14}$ aryl group, a C$_{3-14}$ cycloalkyl group, a 3-14 membered cycloheteroalkyl group, and a 5-14 membered heteroaryl group;
R[3], R[4], R[5], and R[6] independently are H or CN, wherein at least one of R[3], R[4], R[5], and R[6] is CN; and
n is 1, 2, 3, or 4.

36. A composite comprising a substrate and the thin film semiconductor of claim 34 deposited on the substrate.

37. A field effect transistor device comprising the thin film semiconductor of claim 34.

38. A field effect transistor device comprising the composite of claim 36.

39. The field effect transistor device of claim 37 comprising a dielectric material, wherein the dielectric material comprises an organic dielectric material, an inorganic dielectric material, or a hybrid organic/inorganic dielectric material.

40. A photovoltaic device comprising the thin film semiconductor of claim 34.

41. A photovoltaic device comprising the composite of claim 36.

42. The photovoltaic device of claim 40 comprising a p-type semiconducting material adjacent to the thin film semiconductor.

43. An organic light emitting diode device comprising the thin film semiconductor of claim 34.

44. An organic light emitting diode device comprising the composite of claim 36.

45. A unipolar or complementary circuit device comprising the thin film semiconductor of claim 34.

46. A unipolar or complementary circuit device comprising the composite of claim 36.

47. A method of making an article of manufacture of claim 31, said method comprising depositing a composition comprising one or more compounds of formula I dissolved or dispersed in a liquid medium, said one or more compounds of formula I being:

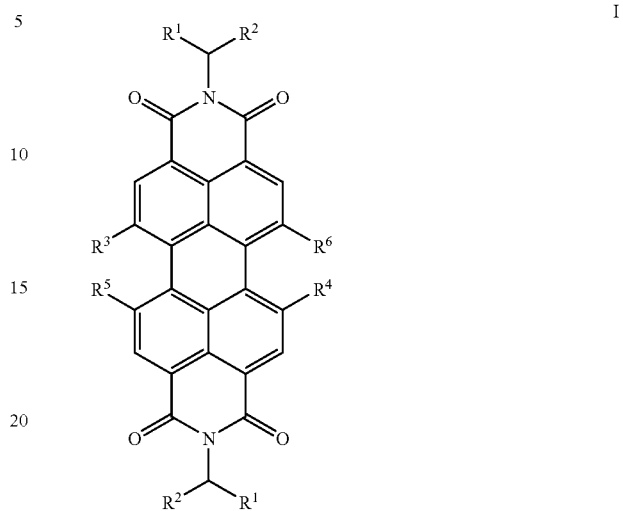

wherein:
R[1] and R[2], at each occurrence, independently are selected from a $C_{1-30}$ alkyl group, a $C_{2-30}$ alkenyl group, a $C_{2-30}$ alkynyl group, a $C_{1-30}$ haloalkyl group, and a 3-22 membered cyclic moiety, each optionally substituted with 1-4 groups independently selected from halogen, —CN, —NO$_2$, —C(O)H, —C(O)OH, —CONH$_2$, —OH, —NH$_2$, —CO(C$_{1-10}$ alkyl), —C(O)OC$_{1-10}$ alkyl, —CONH(C$_{1-10}$ alkyl), —CON(C$_{1-10}$ alkyl)$_2$, —S—C$_{1-10}$ alkyl, —O—(CH$_2$CH$_2$O)$_n$(C$_{1-10}$ alkyl), —NH(C$_{1-10}$ alkyl), —N(C$_{1-10}$ alkyl)$_2$, a C$_{1-10}$ alkyl group, a C$_{2-10}$ alkenyl group, a C$_{2-10}$ alkynyl group, a C$_{1-10}$ haloalkyl group, a C$_{1-10}$ alkoxy group, a C$_{6-14}$ aryl group, a C$_{3-14}$ cycloalkyl group, a 3-14 membered cycloheteroalkyl group, and a 5-14 membered heteroaryl group;
R[3], R[4], R[5], and R[6] independently are H or CN, wherein at least one of R[3], R[4], R[5], and R[6] is CN; and
n is 1, 2, 3, or 4.

48. The method of claim 47, wherein depositing the composition comprises at least one of vacuum vapor deposition, printing, spin coating, drop-casting, zone casting, dip coating, blade coating, and spraying.

49. A compound having the formula:

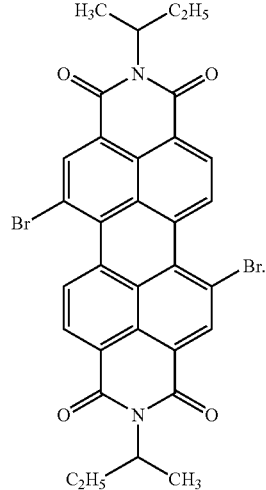 [SMILES: CCC(C)N1C(=O)c2ccc3c4c(Br)cc5c6c(ccc(c7c(Br)cc(c2c37)C1=O)c64)C(=O)N(C(C)CC)C5=O]

50. A compound having the formula:
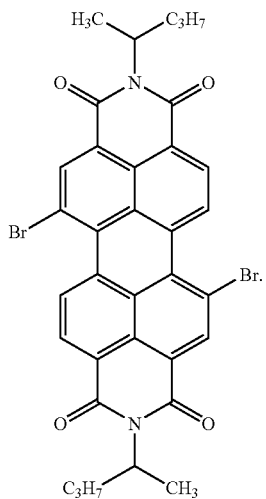
51. A compound having the formula:
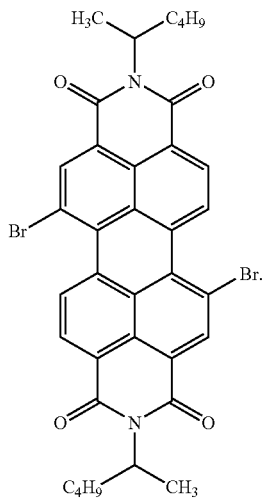
52. A compound having the formula:
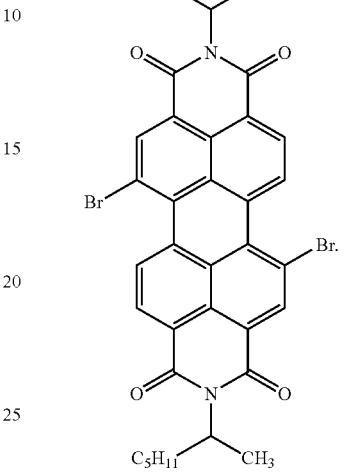
53. A compound having the formula:
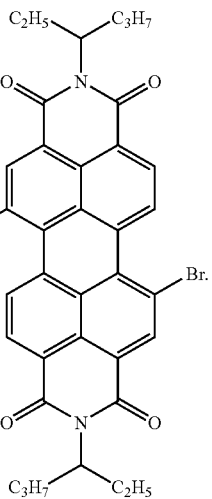

54. A compound having the formula:
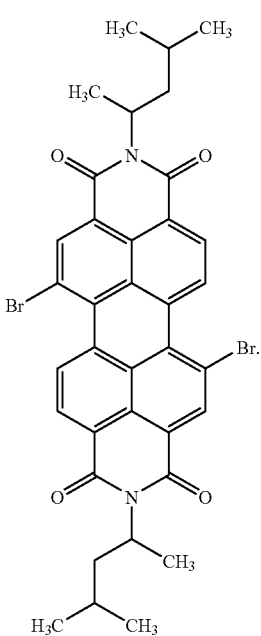 [SMILES: CC(C)CC(C)N1C(=O)c2ccc3c4c(Br)cc5c6c(ccc(c7c(Br)cc(c2c37)C1=O)c64)C(=O)N(C(C)CC(C)C)C5=O]
55. A compound having the formula:
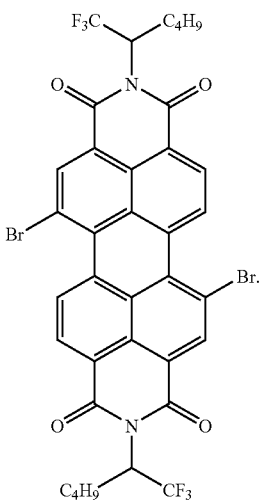
56. A compound having the formula:
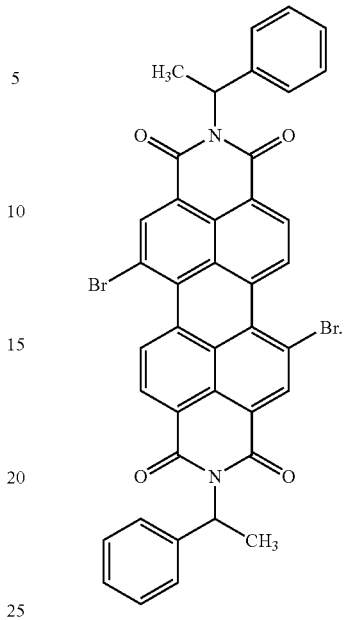
57. A compound having the formula:
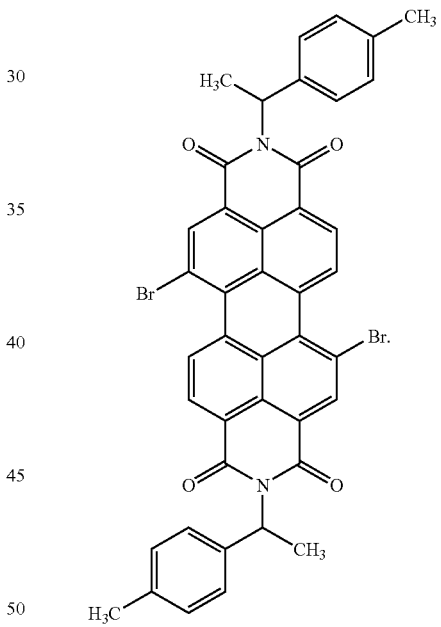
* * * * *